(12) United States Patent
Budde et al.

(10) Patent No.: US 10,655,152 B2
(45) Date of Patent: May 19, 2020

(54) METHOD FOR PRODUCING AN AMIDE

(71) Applicant: SOLENIS TECHNOLOGIES, L.P., Wilmington, DE (US)

(72) Inventors: Michael Budde, Ilvesheim (DE); Michael Braun, Heidelberg (DE); Juergen Daeuwel, Heidelberg (DE); Peter Oedman, Neustadt (DE); Kai-Uwe Baldenius, Mannheim (DE); Matthias Kleiner, Goennheim (DE); Stephan Freyer, Neustadt (DE)

(73) Assignee: SOLENIS TECHNOLOGIES, L.P., Wilmington, DE (US)

( * ) Notice: Subject to any disclaimer, the term of this patent is extended or adjusted under 35 U.S.C. 154(b) by 0 days.

(21) Appl. No.: 15/513,670

(22) PCT Filed: Sep. 30, 2015

(86) PCT No.: PCT/EP2015/072506
§ 371 (c)(1),
(2) Date: Mar. 23, 2017

(87) PCT Pub. No.: WO2016/050816
PCT Pub. Date: Apr. 7, 2016

(65) Prior Publication Data
US 2017/0247726 A1 Aug. 31, 2017

(30) Foreign Application Priority Data
Sep. 30, 2014 (EP) .................................. 14003378

(51) Int. Cl.
C12P 9/00 (2006.01)
C12P 13/02 (2006.01)
C12N 9/78 (2006.01)
C12N 9/80 (2006.01)

(52) U.S. Cl.
CPC ............... *C12P 13/02* (2013.01); *C12N 9/78* (2013.01); *C12N 9/80* (2013.01); *C12Y 305/01004* (2013.01); *C12Y 305/05001* (2013.01)

(58) Field of Classification Search
None
See application file for complete search history.

(56) References Cited

U.S. PATENT DOCUMENTS

| | | | |
|---|---|---|---|
| 4,711,955 A | 12/1987 | Ward et al. | |
| 5,525,711 A | 6/1996 | Hawkins et al. | |
| 5,792,608 A | 3/1998 | Swaminathan et al. | |
| 5,827,699 A | 10/1998 | Yanenko et al. | |
| 2004/0048348 A1 | 3/2004 | Murao et al. | |
| 2007/0077633 A1 | 4/2007 | Armitage et al. | |
| 2007/0077634 A1 | 4/2007 | Hughes et al. | |
| 2009/0269822 A1 | 10/2009 | Hughes et al. | |
| 2011/0008853 A1 | 1/2011 | Armitage et al. | |
| 2011/0104690 A1 | 5/2011 | Huimin et al. | |

FOREIGN PATENT DOCUMENTS

| | | |
|---|---|---|
| AU | 2004245849 B | 10/2008 |
| EP | 0 302 175 A2 | 2/1989 |
| JP | 2013-517777 A | 5/2013 |
| RU | 2008589 C1 | 2/1994 |
| RU | 2304165 C1 | 8/2007 |
| RU | 2403280 C2 | 11/2010 |
| WO | 2005/054456 A1 | 6/2005 |
| WO | 2005/054489 A1 | 6/2005 |
| WO | 2005054456 A | 6/2005 |
| WO | 2005054489 A | 6/2005 |
| WO | 2004245849 B2 | 10/2008 |

OTHER PUBLICATIONS

Brandao et al. (Appl. & Environ. Microbiol., 2003, vol. 69, No. 10, pp. 5754-5766).*
Tauber et al. (Appl. & Environ. Microbiol., 2000, vol. 66, No. 4, pp. 1634-1638).*
Chen et al. (Ad Biochem. Engin./Biotech., 2009, vol. 113, pp. 33-77).*
International Search Report and Written Opinion dated Apr. 15, 2016 in PCT/EP2015/072506 filed Sep. 30, 2015.
Hideaki Yamada et al., "Nitrile Hydratase and Its Application to Industrial Production of Acrylamide", Bioscience Biotechnology Biochemistry, vol. 60, No. 9, 1996, pp. 1391-1400, XP008057288.
Marius Tudorascu et al., "A New Process for Acrylamide Synthesis by Enzymatic Hydrolysis of Acrylonitrile in Disperse System", Revista de Chimie, vol. 60, No. 2, 2009, pp. 197-200, XP002752188.
Yuchao Ma et al., "Identification of nitrile hydratase-producing *Rhodococcus ruber* TH and characterization of an amiE-negative mutant", Bioresource Technology, vol. 101, 2010, pp. 285-291, XP026624004.
Office Action dated Aug. 8, 2018 in Columbian Patent Application No. 9565 (with English translation).
Yamada H et al., "Nitrile hydratase and its application to industrial production of acrylamide", Bioscience Biotechnology Biochemistry (1996), vol. 60, No. 9.

(Continued)

*Primary Examiner* — Hope A Robinson
(74) *Attorney, Agent, or Firm* — Lorenz & Kopf, LLP

(57) ABSTRACT

The present invention relates to means and methods for producing an amide compound from a nitrile compound with less acrylic acid as by-product using a Nitrile hydratase (NHase) and Amidase producing microorganism as biocatalyst. Also provided is an aqueous amide compound obtained by the methods of the invention as well as a composition comprising acrylamide or polyacrylamide as well as a dried microorganism exhibiting a NHase/Amidase activity ratio of at least 400 when being brought into contact with a nitrile compound to convert said nitrile compound into an amide compound.

18 Claims, 7 Drawing Sheets
Specification includes a Sequence Listing.

(56) References Cited

OTHER PUBLICATIONS

Tudorascu M et al., "A new process for acrylamide synthesis by enzymatic hydrolysis of acrylonitrile in disperse sysetm", Revista De Chimie (2009, vol. 60, No. 2, pp. 197-200.
Ma Y et al., "Identification of nitrile hydratase-producing Rhodococcus ruber TH and characterization of an amiE-negative mutant", Bioresource Technology (2010), vol. 101, No. 1, pp. 285-291.
Cantarella, L., et al., "Nitrile, Amide and Temperature Effects on Amidase-Kinetics During Acrylonitrile Bioconversion by Nitrile-Hydratase/Amidase in Situ Cascase System", Bioresource Technology, May 3, 2013, vol. 142, pp. 320-328.
G. Zhao and G. Zhang, "Effect of protective agents, freezing temperature, rehydration media on viability of malolactic bacteria subjected to freeze-drying", Journal of Applied Microbiology, 2005, v. 99, p. 333-338, DOI: 10.1111/.365-2672.2005.02587.x.

\* cited by examiner

METHOD FOR PRODUCING AN AMIDE

The present invention relates to methods for producing an amide compound from a nitrile compound using a Nitrile hydratase (NHase) and Amidase producing microorganism as biocatalyst, which microorganism is pre-treated by a drying step before being contacted with said nitrile compound as well as to uses of such a microorganism for producing an amide compound from a nitrile compound. In addition, the invention is directed to a method for reducing the formation of acrylic acid by-products when producing an amide compound from a nitrile compound by means of a Nitrile hydratase and Amidase producing microorganism as well as to the use of a drying method for increasing the NHase/Amidase or decreasing the Amidase activity of such a microorganism. Also provided is an aqueous amide compound obtained by the methods of the invention as well as a composition comprising acrylamide or polyacrylamide as well as a dried microorganism exhibiting a NHase/Amidase activity ratio of at least 400 when being brought into contact with a nitrile compound to convert said nitrile compound into an amide compound.

Acrylamide is used as a monomer to form polymers and copolymers of acrylamide. For these polymerization and copolymerization reactions aqueous acrylamide solutions prepared by bioconversion can be used. However, it has been found that high acrylic acid contents within acrylamide solutions lead to reduced performance of the resulting acrylamide polymers and copolymers. More specifically, the presence of acrylic acid can significantly impair the physical properties of the acrylamide polymer and copolymer material, which leads to a reduced solubility and performance in various applications such as water treatment, paper making, oil recovery or mining.

Since the discovery of nitrile hydratase (NHase), a microbial enzyme that hydrolyses nitriles to amides, microorganisms having NHase activity have been intensively used for the industrial production of amide compounds. Due to milder reaction conditions compare to the chemical synthesis of amides, the use of NHase producing microorganisms as biocatalysts is more and more on the rise.

In fact, one of the most well-known commercial examples of nitrile bioconversion by NHase producing microorganisms is the manufacture of acrylamide from acrylonitrile.

However, a challenging problem in the use of NHase producing microorganisms as biocatalysts, is the occurrence of a side reaction mediated by the enzyme amidase. While NHase hydrolyses a nitrile compound to the corresponding amide compound, Amidase further converts the amide compound into the corresponding carboxylic acid, particularly into acrylic acid.

The technical problem underlying the present invention is to solve problems occurring due to the formation of acrylic acids as byproducts in the production of amide compounds from nitrile compounds using NHase and Amidase producing microorganisms as biocatalysts.

The technical problem is solved by providing the embodiments reflected in the claims, described in the description and illustrated in the examples and figures that follow.

Much to their surprise, the present inventors found that carboxylic acid production, particularly acrylic acid production as by-product in the bioconversion of a nitrile compound to an amide compound is much decreased when the microorganism which produces Nitrile hydratase (NHase) and Amidase and which serves as biocatalyst for the bioconversion is pre-treated by a drying step before being contacted with the nitrile compound. Without being bound by theory, it appears that, because of the drying step to which such a microorganism is subjected, the Amidase activity may be decreased, thereby reducing the production of acrylic acid from amide which is produced by the activity of NHase. In other words, such a dried microorganism seems to have a ratio between NHase activity and Amidase activity which is more in favor of NHase activity, i.e., the ratio NHase activity to Amidase activity is >1.0, such as at least >10, >50, >100, >200, >300 or >400.

In fact, as demonstrated in the appended Examples, it is apparent that a microorganism which was pre-treated by a drying step before being contacted with a nitrile compound which is then subject to bio-conversion by said microorganism has the highest value as regards NHase/Amidase activity. Given the fact that the setting up contained almost equal amounts of the biocatalyst (reflected by "NHase activity in the setting up", see Table 1 and 2), it is apparent that the drying step, i.e. subjecting a biocatalyst to a drying step before bringing it into contact with a nitrile compound significantly influences the amount of the by-product acrylic acid. This means that because of the drying step, the Amidase activity is reduced to such an extent that such dried microorganisms produce an amide compound with less acrylic acid as by-product which is apparent from the outermost right column. In sum, since reaction parameters are kept equal between the different setting ups, it is apparent that the improvement in reducing the amount of acrylic acid can be ascribed to the drying step.

Accordingly, the present invention relates to a method for producing an amide compound from a nitrile compound, comprising contacting a nitrile compound with a Nitrile hydratase (NHase) and Amidase producing microorganism, wherein said microorganism is pre-treated by a drying step before being contacted with said nitrile compound.

The present invention also provides a method for producing an amide compound from a nitrile compound, comprising the steps of (a) drying a NHase and Amidase producing microorganism; and (b) contacting a nitrile compound with said microorganism.

Furthermore, in line with the surprising finding of the present inventions, herein is provided is a method for reducing the formation of acrylic acid when producing an amide compound from a nitrile compound, comprising contacting acrylonitrile with a NHase and Amidase producing microorganism, wherein said microorganisms is the one as defined herein.

Also provided is a method for producing a microorganism with an increased NHase/Amidase activity ratio, comprising drying a NHase and Amidase producing microorganism.

Likewise, a method for producing a microorganism with a decreased Amidase activity, comprising drying a NHase and Amidase producing microorganism is provided herein.

Furthermore, the present invention provides a use of a NHase and Amidase producing microorganism as defined herein for producing an amide compound from a nitrile compound.

Similarly, the present invention provides a use of a drying method for increasing the NHase/Amidase activity ratio of a NHase and Amidase producing microorganism or, in the alternative or in addition, provides a use of a drying method for decreasing the Amidase activity of a NHase and Amidase producing microorganism.

Since the amide solution, in line with the findings of the present inventors, contains less acrylic acid as by-product of the conversion of a nitrile compound into an amide compound, the present invention provides an aqueous amide compound solution obtained by the methods of the present invention.

Further in line with the present inventors' finding, herein is provided a composition comprising acrylamide or polyacrylamide and a NHase and Amidase producing microorganism, said microorganism preferably exhibiting an NHase/Amidase activity ratio of at least 400.

The present invention will in the following be described in detail with reference to several exemplary embodiments. Numerous specific details will be set forth in order to provide a thorough understanding of embodiments of the present invention. When further defining and specifying single features of the methods, compositions or uses according to the present invention, such definitions and specifications apply to all, the inventive methods, the inventive compositions and the inventive uses as described and provided herein.

Furthermore, it will be apparent, to one skilled in the art, that embodiments may be practiced without some or all of specific details set forth in the following. In other instances, well known process steps have not been described in detail in order to not unnecessarily obscure the present invention.

As has turned out in line with the findings of the present invention, a NHase and Amidase producing microorganism is able to convert a nitrile compound into an amide compound, but does—in contrast to other such NHase and Amidase producing microorganisms—produce less carboxylic acid, particularly acrylic acid when said microorganism is pre-treated by a drying step before it is brought into contact with the nitrile compound that should be subject to the bioconversion into an amide compound. This property of such a dried microorganism is advantageous, since particularly acrylic acid causes problems in a subsequent polymerization reaction from amide to polyacrylamide. It is thus an outstanding achievement by the present inventors to provide a biocatalyst in the form of a microorganism which has a low Amidase activity, while its NHase activity is essentially unaltered such that the microorganism produces an amide compound with a low amount/concentration of a carboxylic acid, particularly acrylic acid. Of note, the present inventors reached this achievement without genetically engineering an NHase and Amidase producing microorganism or subjecting such a microorganism to mutagenizing agents or the like or without excessive screening for such a (by chance) naturally-occurring microorganism, but by thoughtful observing that subjecting an NHase and Amidase producing microorganism to a drying step before contacting said microorganism with a nitrile compound in the course of its bioconversion into an amide compound.

Accordingly, the present invention provides a method for producing an amide compound from a nitrile compound, comprising contacting a nitrile compound with a Nitrile hydratase (NHase) and Amidase producing microorganism, wherein said microorganism is pre-treated by a drying step before being contacted with said nitrile compound.

Also, the present invention provides a method for producing an amide compound from a nitrile compound, comprising the steps of: (a) drying a NHase and Amidase producing microorganism; and (b) contacting a nitrile compound with said microorganism.

Furthermore, the present invention provides dried microorganisms which are able to produce NHase and Amidase, whereby the ratio between NHase and Amidase activity is >1.0, such as at least >10, >50, >100, >200, >300 or >400, said dried microorganisms are capable of producing an amide compound with much less acrylic acid as by-product when compared to the same microorganism which is not dried before being contacted with the nitrile compound that should be (bio-)converted into an amide compound.

The term "pre-treated by a drying step before being contacted" means that a microorganism is treated by means and/or methods for drying said microorganism before it is applied in any of the methods and uses of the present invention. Particularly, a microorganism is dried before it is contacted with a nitrile compound which should be (bio-)converted by said microorganism. Accordingly, a preferred microorganism of the present invention is dried (is subject to a drying step) before it is being contacted (or brought into contact) with a nitrile compound which should be (bio-)converted by said dried microorganism into an amide compound. Preferably, the drying step results in a microorganism having a residual water content of at most 30, 25, 15, 14, 13, 12, 11, 10, 9, 8, 7, 6, or 5 weight percentages (% w/w) of the total mass of the microorganism. The "total mass of the microorganism" is thereby not necessarily limited to the mass of the microorganism as such (although this is of course possible e.g. when the microorganisms have been washed with water before the drying step) but may further include ingredients whose presence may be ascribed to the cultivation of the microorganisms and/or washing steps etc. What follows is that the "total mass of the microorganism" may further include (in addition to the microorganism) residual amount of storage buffer components/salts such as TRIS-based buffers, Saline based buffers etc. and/or residual amounts of the culture medium, growing medium, nutrient solutions, fermentation broths for example the fermentation broth that was used to culture the microorganisms etc., stabilizers, additives (e.g. drying additives) etc.

The term "microorganism(s)", when used herein encompasses "Nitrile hydratase and Amidase producing microorganism(s)", or alternatively "NHase and Amidase producing microorganism(s)". A microorganism in the context of the present invention is preferably a bacterium, fungus or yeast. A microorganism of the present invention is preferably pre-treated by a drying step before being contacted with a nitrile compound that is subject to bioconversion by said microorganism into an amide compound. A microorganism of the present invention is preferably not immobilized before being dried. "Immobilized" as used herein refers to any immobilization technique known to the person skilled in the art, including, without limitation, binding or adsorbing the microorganism to a support matrix, entrapping or encapsulating the microorganism in a support matrix.

Within the present invention "NHase and Amidase producing microorganisms" are used, or are for use, as a biocatalyst for converting a nitrile compound into the corresponding amide compound. As mentioned, such microorganisms are preferably pre-treated by a drying step before being contacted with a nitrile compound that is subject to bioconversion into an amide compound. As a result, such microorganisms are capable of producing an amide compound with much less acrylic acid as by-product when compared to the same microorganism with was is not dried before being contacted with the nitrile compound that should be converted into an amide compound.

A "nitrile compound" is converted by a microorganism of the present invention into an amide compound by the action of NHase. A nitrile compound is any organic compound that has a —C≡N functional group. A preferred nitrile compound is acrylonitrile. It is also envisaged to use methacrylonitrile, acetonitrile or 3-cyanopyridine in the methods disclosed herein.

An "amide compound" is converted by Amidase into an amide compound. An amide compound has the functional group $R_nC(O)_xNR'_2$, wherein R and R' refer to H or organic groups. For organic amides n=1, x=1. An example of an amide compound is acrylamide. Further examples for amide compounds which are envisaged with regard to the methods of the present invention are methacrylamide, acetamide or nicotinamide.

Within the present invention, a "NHase and Amidase producing microorganism" may be any microorganism which is able to produce the enzymes NHase and Amidase. With this regard, it is not relevant for the present invention whether the microorganism naturally encodes NHase and Amidase or whether it has been genetically modified to encode said enzymes. Furthermore, the biocatalyst may be a microorganism which naturally encodes NHase and Amidase and which is further genetically engineered, e.g., to increase production of NHase, or to increase stability and/or export of NHase or to decrease production of Amidase, or to increase stability and/or export of Amidase.

In the context of the present invention, "NHase and Amidase producing microorganisms" which are not naturally encoding NHase may be genetically engineered microorganisms which naturally do not contain a gene encoding a NHase, but which have been manipulated such as to contain a polynucleotide encoding a NHase (e.g., via transformation, transduction, transfection, conjugation, or other methods suitable to transfer or insert a polynucleotide into a cell as known in the art; cf. Sambrook and Russell 2001, Molecular Cloning: A Laboratory Manual, CSH Press, Cold Spring Harbor, N.Y., USA), thus enabling the microorganisms to produce and stably maintain the NHase enzyme. For this purpose, it may further be required to insert additional polynucleotides which may be necessary to allow transcription and translation of the NHase gene or mRNA, respectively. Such additional polynucleotides may comprise, inter alia, promoter sequences, or replication origins or other plasmid-control sequences. In this context, such genetically engineered microorganisms which naturally do not contain a gene encoding a NHase but which have been manipulated such as to contain a polynucleotide encoding a NHase may be prokaryotic or eukaryotic microorganisms. Examples for such prokaryotic microorganisms include, e.g., representatives of the species *Escherichia coli*. Examples for such eukaryotic microorganisms include, e.g., yeast (e.g., *Saccharomyces cerevisiae*).

Likewise, "NHase and Amidase producing microorganisms" which are not naturally encoding Amidase may be genetically engineered microorganisms which naturally do not contain a gene encoding an Amidase but which have been manipulated such as to contain a polynucleotide encoding an Amidase (e.g., via transformation, transduction, transfection, conjugation, or other methods suitable to transfer or insert a polynucleotide into a cell as known in the art; cf. Sambrook and Russell 2001, Molecular Cloning: A Laboratory Manual, CSH Press, Cold Spring Harbor, N.Y., USA), thus enabling the microorganisms to produce and stably maintain the Amidase enzyme. For this purpose, it may further be required to insert additional polynucleotides which may be necessary to allow transcription and translation of the Amidase gene or mRNA, respectively. Such additional polynucleotides may comprise, inter alia, promoter sequences, or replication origins or other plasmid-control sequences. In this context, such genetically engineered microorganisms which naturally do not contain a gene encoding an Amidase but which have been manipulated such as to contain a polynucleotide encoding an Amidase may be prokaryotic or eukaryotic microorganisms. Examples for such prokaryotic microorganisms include, e.g., representatives of the species *Escherichia coli*. Examples for such eukaryotic microorganisms include, e.g., yeast (e.g., *Saccharomyces cerevisiae*).

"NHase and Amidase producing microorganisms" which (naturally or non-naturally) encode NHase are generally also capable of producing and stably maintaining NHase. However, in accordance with the present invention, it is also possible that such microorganisms only produced NHase during cultivation (or fermentation) of the microorganisms—thus then containing NHase—when being dried and/or being contacted with the nitrile compound. In such a case, it is possible that the microorganisms do not produce NHase during the methods described and provided herein any more, but they act only via the NHase units which they have produced before the drying and which they still contain after the drying. As readily understood by the person skilled in the art, it is also possible that some NHase molecules may leave the microorganism (e.g., due to lysis of the microorganism) and act freely in the solution as biocatalyst.

Likewise, "NHase and Amidase producing microorganisms" which (naturally or non-naturally) encode Amidase are generally also capable of producing and stably maintaining Amidase. However, in accordance with the present invention, it is also possible that such microorganisms only produced Amidase during cultivation (or fermentation) of the microorganisms—thus then containing Amidase—when being dried and/or being contacted with the nitrile compound. In such a case, it is possible that the microorganisms do not produce Amidase during the methods described and provided herein any more, but they act only via the Amidase units which they have produced before the drying and which they still contain after the drying.

In context with the present invention, "NHase and Amidase producing microorganisms" naturally encoding NHase and Amidase, include, inter alia, bacteria of the genus *Rhodococcus, Aspergillus, Acidovorax, Agrobacterium, Bacillus, Bradyrhizobium, Brevibacterium, Burkholderia, Escherichia, Geobacillus, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Comomonas*, and *Pyrococcus*. In preferred embodiments of the invention, the microorganism is selected from bacteria of the genus *Rhodococcus, Pseudomonas, Escherichia* and *Geobacillus*.

In particular, "NHase and Amidase producing microorganism" include, inter alia inter alia, the following species *Rhodococcus rhodochrous, Rhodococcus pyridinovorans, Rhodococcus erythropolis, Rhodococcus equi, Rhodococcus ruber, Rhodococcus opacus, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus* sp BR449, *Bradyrhizobium oligotrophicum, Bradyrhizobium diazoefficiens, Bradyrhizobium japonicum, Burkholderia cenocepacia, Burkholderia gladioli, Escherichia coli, Geobacillus* sp. RAPc8, *Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putid, Rhizobium, Rhodopseudomonas palustris, Serratia liquefaciens, Serratia marcescens, Amyco-* latopsis, *Arthrobacter, Brevibacterium* sp CH1, *Brevibacterium* sp CH2, *Brevibacterium* sp R312, *Brevibacterium imperiale, Corynebacterium nitrilophilus, Corynebacterium pseudodiphteriticum, Corynebacterium glutamicum, Corynebacterium hoffmanii, Microbacterium imperiale, Microbacterium smegmatis, Micrococcus luteus, Nocardia globerula, Nocardia rhodochrous, Pseudonocardia thermophila, Trichoderma, Myrothecium verrucaria, Aureobasidium pullulans, Candida famata, Candida guilliermondii, Candida tropicalis, Cryptococcus flavus, Cryptococcus* sp UFMG-Y28, *Debaryomyces hanseii, Geotrichum candidum, Geotrichum* sp JR1, *Hanseniaspora, Kluyveromyces thermotolerans, Pichia kluyveri, Rhodotorula glutinis, Comomonas testosterone, Pyrococcus abyssi, Pyrococcus furiosus, Pyrococcus horikoshii, Brevibacterium casei,* or *Nocardia* sp. 163.

In preferred embodiments of the invention the "NHase and Amidase producing microorganism" is a bacterium of the species *Rhodococcus rhodochrous* or *Rhodococcus pyridinovorans*. Preferred representatives of these species are *Rhodococcus rhodochrous* (NCIMB 41164), *Rhodococcus rhodochrous* (FERM BP-1478), *Rhodococcus rhodochrous* M8, and *Rhodococcus rhodochrous* M33.

In context of the present invention, "Nitrile hydratase" ("NHase") refers to a microbial enzyme that catalyzes the hydration of nitriles to their corresponding amides (IUBMB Enzyme Nomenclature EC 4.2.1.84. However, the terms "Nitrile hydratase" and "NHase" as used herein also encompass modified or enhanced enzymes which are, e.g., capable of converting a nitrile compound (e.g. acrylonitrile) to an amide compound (e.g. acrylamide) more quickly, or which can be produced at a higher yield/time-ratio, or which are more stable, as long as they are capable to catalyze conversion (i.e. hydration) of a nitrile compound (e.g. acrylonitrile) to an amide compound (e.g. acrylamide).

Methods for determining the ability of a given biocatalyst (e.g. "NHase and Amidase producing microorganism") to convert acrylonitrile to acrylamide are well known in the art. As an example, in context with the present invention, activity of a given biocatalyst to be capable of converting acrylonitrile to acrylamide in the sense of the present invention may be determined as follows: First reacting 100 µl of a cell suspension, cell lysate, dissolved enzyme powder or any other preparation containing the supposed nitrile hydratase with 875 µl of an 50 mM potassium phosphate buffer and 25 µl of acrylonitrile at 25° C. on an eppendorf tube shaker at 1,000 rpm for 10 minutes. After 10 minutes of reaction time, samples may be drawn and immediately quenched by adding the same volume of 1.4% hydrochloric acid. After mixing of the sample, cells may be removed by centrifugation for 1 minute at 10,000 rpm and the amount of acrylamide formed is determined by analyzing the clear supernatant by HPLC. For affirmation of an enzyme to be a nitrile hydratase in context with the present invention, the concentration of acrylamide shall be between 0.25 and 1.25 mmol/l—if necessary, the sample has to be diluted accordingly and the conversion has to be repeated. The enzyme activity may then be deduced from the concentration of acrylamide by dividing the acrylamide concentration derived from HPLC analysis by the reaction time, which has been 10 minutes and by multiplying this value with the dilution factor between HPLC sample and original sample. Activities >5 U/mg dry cell weight, preferably >25 U/mg dry cell weight, more preferably >50 U/mg dry cell weight, most preferably >100 U/mg dry cell weight indicate the presence of a functionally expressed nitrile hydratase and are considered as nitrile hydratase in context with the present invention.

In context with the present invention, the nitrile hydratase may be a polypeptide encoded by a polynucleotide which comprises or consists of a nucleotide sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the nucleotide sequence of SEQ ID NO: 1 (alpha-subunit of nitrile hydratase of *R. rhodochrous*: GTGAGCGAGCACGT-CAATAAGTACACGGAGTACGAGGCACGTAC-CAAGGCGATCGAAACC TTGCTGTACGAGC-GAGGGCTCATCACGCCCGCCGCGGTCGACCGAGT CGTTTCGTACTAC GAGAACGAGATCGGC-CCGATGGGCGGTGCCAAGGTCGTGGCCAAGTC-CTGGGTGGACCC TGAGTACCGCAAGTGGCTC-GAAGAGGACGCGACGGCCGCGATGGCGTCATTGG GCTATG CCGGTGAGCAGGCACACCAAATTTCG-GCGGTCTTCAACGACTCCCAAACGCATCACGTGG TGGTGTGCACTCTGTGTTCGTGCTATCCGTGGCCG-GTGCTTGGTCTCCCGCCCGCCTGGT ACAAGAG-CATGGAGTACCGGTCCCGAGTGGTAGCGGAC-CCTCGTGGAGTGCTCAAGCGC GATTTCGGTTTCGACATCCCCGATGAGGTGGAG-GTCAGGGTTTGGGACAGCAGCTCCGAA ATCCGC-TACATCGTCATCCCGGAACGGCCGGCCGGCAC-CGACGGTTGGTCCGAGGAGGA GCTGACGAAGCTGGTGAGCCGGGACTCGAT-GATCGGTGTCAGTAATGCGCTCACACCGCA GGAAGTGATCGTATGA) and/or to the nucleotide sequence of SEQ ID NO: 3 (beta-subunit of nitrile hydratase of *R. rhodochrous*: ATGGATGGTATCCACGACACAG-GCGGCATGACCGGATACGGACCGGTCCCCTATCA-GAAG GACGAGCCCTTCTTCCACTAC-GAGTGGGAGGGTCGGACCCTGTCAATTCTGACTTG GATG CATCTCAAGGGCATATCGTGGTGGGA-CAAGTCGCGGTTCTTCCGGGAGTCGATGGGGAAC GAAAACTACGTCAACGAGATTCGCAACTCGTACTA-CACCCACTGGCTGAGTGCGGCAGAA CGTATC-CTCGTCGCCGACAAGATCATCACCGAAGAAGAGC-GAAAGCACCGTGTGCAAGAG ATCCTTGAGGGTCGGTACACGGACAGGAAGC-CGTCGCGGAAGTTCGATCCGGCCCAGAT CGA-GAAGGCGATCGAACGGCTTCACGAGCCCCACTC-CCTAGCGCTTCCAGGAGCGGAGC CGAGTTTCTCTCTCGGTGACAAGATCAAAGT-GAAGAGTATGAACCCGCTGGGACACACAC GGTGC-CCGAAATATGTGCG-GAACAAGATCGGGGAAATCGTCGCCTACCACGGCT GCCAGA TCTATCCCGAGAGCAGCTCCGCCGGC-CTCGGCGACGATCCTCGCCCGCTCTACACGGTC GCGTTTTCCGCCCAGGAACTGTGGGGCGACACG-GAAACGGGAAAGACGTAGTGTGCGT CGATCTCTGGGAACCGTACCTGATCTCTGCGTGA), provided that the polypeptide encoded by said polynucleotide is capable of catalyzing hydration of acrylonitrile to acrylamide (i.e. has nitrile hydratase activity) as described and exemplified herein. Also in the context with the present invention, the nitrile hydratase may be a polypeptide which comprises or consists of an amino acid sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the amino acid sequence of SEQ ID NO: 2 (alpha-subunit of nitrile hydratase of *R. rhodochrous*: VSEHVNKYTE YEARTKAIET LLYERGLITP AAVDRVVSYY ENEIGPMGGA KVVAKSWVDP EYRKWLEEDA TAAMASLGYA GEQAHQISAV FNDSQTHHVV VCTLCSCYPW PVLGLPPAWY KSMEYRSRVV ADPRGVLKRD FGFDIPDEVE VRVWDSSSEI RYIVIPERPA GTDGWSEEEL TKLVSRDSMI GVSNALTPQE VIV) and/or to the amino acid sequence of SEQ ID NO: 4 (beta-subunit of nitrile hydratase of *R. rhodochrous*: MDGIHDTGGM TGYGPVPYQK DEPFFHYEWE GRTLSILTWM HLKGISWWDK SRFFRESMGN ENYVNEIRNSY YTHWLSAAE RILVADKIIT EEERKHRVQE ILEGRYTDRK PSRKFDPAQI EKAIERLHEP HSLALPGAEP SFSLGDKIKV KSMNPLGHTR CPKYVRNKIG EIVAYHGCQI YPESSSAGLG DDPRPLYTVA FSAQELWGDD GNGKDVVCVD LWEPYLISA), provided that said polypeptide is capable of catalyzing hydration of acrylonitrile to acrylamide as described and exemplified herein.

The level of identity between two or more sequences (e.g., nucleic acid sequences or amino acid sequences) can be easily determined by methods known in the art, e.g., by BLAST analysis. Generally, in context with the present invention, if two sequences (e.g., polynucleotide sequences or amino acid sequences) to be compared by, e.g., sequence comparisons differ in identity, then the term "identity" may refer to the shorter sequence and that part of the longer sequence that matches said shorter sequence. Therefore, when the sequences which are compared do not have the same length, the degree of identity may preferably either refer to the percentage of nucleotide residues in the shorter sequence which are identical to nucleotide residues in the longer sequence or to the percentage of nucleotides in the longer sequence which are identical to nucleotide sequence in the shorter sequence. In this context, the skilled person is readily in the position to determine that part of a longer sequence that matches the shorter sequence. Furthermore, as used herein, identity levels of nucleic acid sequences or amino acid sequences may refer to the entire length of the respective sequence and is preferably assessed pair-wise, wherein each gap is to be counted as one mismatch. These definitions for sequence comparisons (e.g., establishment of "identity" values) are to be applied for all sequences described and disclosed herein.

Moreover, the term "identity" as used herein means that there is a functional and/or structural equivalence between the corresponding sequences. Nucleic acid/amino acid sequences having the given identity levels to the hereindescribed particular nucleic acid/amino acid sequences may represent derivatives/variants of these sequences which, preferably, have the same biological function. They may be either naturally occurring variations, for instance sequences from other varieties, species, etc., or mutations, and said mutations may have formed naturally or may have been produced by deliberate mutagenesis. Furthermore, the variations may be synthetically produced sequences. The variants may be naturally occurring variants or synthetically produced variants or variants produced by recombinant DNA techniques. Deviations from the above-described nucleic acid sequences may have been produced, e.g., by deletion, substitution, addition, insertion and/or recombination. The term "addition" refers to adding at least one nucleic acid residue/amino acid to the end of the given sequence, whereas "insertion" refers to inserting at least one nucleic acid residue/amino acid within a given sequence. The term "deletion" refers to deleting or removal of at least one nucleic acid residue or amino acid residue in a given sequence. The term "substitution" refers to the replacement of at least one nucleic acid residue/amino acid residue in a given sequence. Again, these definitions as used here apply, mutatis mutandis, for all sequences provided and described herein.

Generally, as used herein, the terms "polynucleotide" and "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules which can serve as primers.

"Amidase" refers to a microbial enzyme that catalyzes the hydrolysis of amides to their corresponding carboxylic acids (IUBMB Enzyme Nomenclature EC 3.5.1.4. "Amidase"). Amidase preferably refers herein to an Amidase that is co-expressed with a NHase and which converts the amide produced by the NHase further to the corresponding carboxylic acid. The term "Amidase" as used herein also encompasses modified or impaired enzymes as long as such enzymes still have Amidase activity.

Without being bound by theory, it is believed that drying of the biocatalyst (i.e. microorganism) decreases the activity of Amidase, whereby the NHase activity is thought to decrease to a lower extent or remains unchanged. In fact, the present inventors observed that the activity of NHase was higher than the activity of Amidase, when the NHase and Amidase producing microorganism was pre-treated by a drying step before being contacted with a nitrile compound that should be subject to bioconversion (nitrile compound into amide compound) by said microorganism.

As mentioned above, it was observed by the present inventors that a microorganism when pre-treated with a drying step before contacted with a nitrile compound that should be converted by said microorganism into an amide compound, said microorganism is capable of producing an amide compound with less acrylic acid when compared to the same microorganism that was not pre-treated by a drying step before being contacted with said nitrile compound.

Accordingly, a microorganism of the present invention has preferably a NHase/Amidase activity ratio of at least 400 Units. NHase activity is preferably determined as described herein above.

Also in accordance with the findings of the present invention, the contacting step referred to in the methods of the present invention is conducted with a dried microorganism. According to an embodiment, the contacting step referred to in the methods of the present invention is conducted with a reconstituted microorganism. A reconstituted microorganism is a dried microorganism that is suspended, i.e. present in a slurry or dissolved in an aqueous solution such as water or a buffer solution having a physiologic pH, or aqueous composition. The latter may contain one or more further ingredients such as glucose. Reconstitution refers herein to the addition of an aqueous composition to the dried microorganism before the microorganism is contacted with the nitrile compound. Accordingly, in any one of the methods described herein, the contacting step may be conducted with a dried microorganism that is suspended in an aqueous composition. Such aqueous compositions include, without limitation, water (e.g. deionized water), and a buffer (e.g. phosphate buffer).

Given the above, it is preferred that the contacting step referred to in the methods of the present invention is conducted with a microorganism that is in the form of a powder, granule, and/or suspension. It is also possible to use a matrix-bound microorganism for conducting the contacting step.

As explained above, the ratio of NHase activity to Amidase activity of a microorganism of the present invention which is also applied in the methods and uses described herein is increased when compared to a reference microorganism.

In fact, as shown in the appended Examples, it is apparent that that a microorganism which was pre-treated by a drying step before being contacted with a nitrile compound, which is then subject to bio-conversion by said microorganism, has the lowest acrylic acid value in comparison to microorganisms which are not pre-treated by a drying step. This finding implies that the Amidase activity of a dried microorganism seems to be reduced or impaired, since non-dried microorganisms produce more acrylic acid as by-product, whereby acrylic acid results from the conversion of an amide compound into acrylic acid. As a result, the NHase activity is—relative to the (decreased) Amidase activity—increased. Indeed, because of the drying step, the Amidase activity is reduced to such an extent that such dried microorganisms produce an amide compound with less acrylic acid as by-product which is apparent from the outermost right column in Table 1 and 2. In sum, since reaction parameters as applied in Examples 1 and 2 are kept equal between the different setting ups, it is apparent that the improvement in reducing the amount of acrylic acid can be ascribed to the drying step.

As a "reference microorganism" when referred to herein a non-dried biocatalyst (i.e. microorganism) may be used. Accordingly, a reference microorganism is one which was not pre-treated by a drying step before being contacted with a nitrile compound that should be converted into an amide compound by a microorganism of the present invention which is pre-treated by a drying step before being contacted with said nitrile compound. A suitable "reference microorganism" is for example a non-dried microorganism of the same strain as the microorganism used as biocatalyst in the method(s) of the invention. Furthermore, the "reference microorganism" may correspond to the biocatalyst (i.e. microorganism) used in the method of the invention before drying. In this case one may determine the NHase/Amidase activity of microorganism used as biocatalyst before and after the drying step a) of the method and compare both NHase/Amidase activities in order to determine whether the drying increases the NHase/Amidase activity of the microorganism. Moreover, *Rhodococcus rhodochrous* (NCIMB 41164) may be used as a "reference microorganism". In order to determine whether the drying process carried out in step a) increases the NHase/Amidase activity ratio of the used microorganism one may additionally or alternatively subject *Rhodococcus rhodochrous* (NCIMB 41164) to the drying process carried out in step a). In case the NHase/Amidase activity ratio of *Rhodococcus rhodochrous* (NCIMB 41164) is increased by the drying carried out in step a), it must be assumed that the NHase/Amidase activity ratio of the microorganism used as biocatalyst in the method of the invention is likewise decreased by the drying carried out in step a).

Within the present invention, the microorganism is preferably not cultivated between the drying of the microorganism and contacting of the dried microorganism with the nitrile compound. "Cultivated", as used herein, means that the microorganism is suspended in a culture medium and kept under conditions allowing the microorganism to grow.

Between drying of the microorganism and contacting of the dried microorganism with the nitrile compound, the microorganism is preferably kept under conditions which inhibit that the microorganism regains its NHase/Amidase activity ratio before drying.

The increase in the ratio of NHase activity to Amidase activity $$\left(\frac{NHase \text{ activity (in Units)}}{Amidase \text{ activity (in Units)}}\right)$$

is preferably by a factor of at least 1.4 or more, such as 1.5, 1.6, 1.7, 1.8, 1.9, 2.0, 2.1, 2.2, 2.3, 2.4 or 2.5, or even more.

Similarly, the decrease in the ratio of Amidase activity to NHase activity $$\left(\frac{Amidase \text{ activity (in Units)}}{NHase \text{ activity (in Units)}}\right)$$

is preferably by a factor of at least 0.7 or less, such as 0.6, 0.5, 0.4, 0.3, 0.2, or 0.1, or even less.

In accordance with the findings of the present invention a method for producing an amide compound from a nitrile compound, comprising the steps of: (a) drying a NHase and Amidase producing microorganism; and (b) contacting a nitrile compound with said microorganism is provided.

Step (a), without being bound by theory, is assumed to increase the ratio of NHase activity to Amidase activity $$\left(\frac{NHase \text{ activity (in Units)}}{Amidase \text{ activity (in Units)}}\right).$$

NHase activity is measured and determined in accordance with the general knowledge of a skilled artisan, e.g. as described herein above.

Similarly, Amidase activity is measured and determined in accordance with the general knowledge of a skilled artisan, e.g. Amidase activity can be assayed at room temperature by measuring the ammonia liberated from acrylamide degradation at 630 nm.

Accordingly, as described herein, drying of a microorganism employed as biocatalyst increases the NHase/Amidase activity ratio of said microorganism. Preferably, drying is mediated by spray drying, freeze-drying, heat drying, air drying, vacuum drying, fluidized-bed drying and/or spray granulation. With this respect, spray drying and freeze drying are preferred, since in general by using a biocatalyst, which has been subjected to spray- or freeze drying, a higher reduction of the acrylic acid formation in the during production of an amide compound from a nitrile compound is achieved compared to employing a microorganism which has been dried using other methods. In any one of the methods described herein drying of the microorganism may be carried out immediately before the dried microorganism is contacted with the nitrile compound. Alternatively, the microorganism may be stored between drying and contacting of the dried microorganism with the nitrile compound. For storing the microorganism between the drying and the contacting step the dried microorganism may be kept in a dry state (i.e. the microorganism is not reconstituted), may be frozen, may be protected from heat, may be protected from moisture and/or may not be cultivated.

There is no particular limitation on the form of the dried microorganism at the moment when the dried microorganism is contacted with the nitrile compound. The dried microorganism may be dry and/or in the form of a drying product achievable by any of the drying methods described herein, such as spray-drying or freeze drying. Accordingly, in any one of the methods and further embodiments described herein, the contacting step may be conducted with a microorganism having a residual water content of at most 30, 25, 15, 14, 13, 12, 11, 10, 9, 8, 7, 6 or 5 weight percentages (% w/w) of the total mass of the microorganism. Methods of determining the residual water content are familiar to the skilled person. For example, in the context of the present invention the residual water content of a sample of the dried microorganism may be determined via thermogravimetric analysis. At the beginning of the thermogravimetric analysis the initial weight of the sample is determined. The sample is then heated and the water vaporizes. Heating is continued until the sample weight remains constant. The difference between the constant weight at the end of the analysis and the initial weight represents the amount of water vaporized during the analysis, which allows for calculation of the residual water content of the sample. For determination of the residual water content via thermogravimetric analysis, the sample of the microorganism may be, for example, analyzed on a 'Mettler Toledo HB43-S Halogen moisture analyzer', operated at 130° C. until the sample weight remains constant for at least 30 seconds. The "total mass of the microorganism" is thereby not necessarily limited to the mass of the microorganism as such (although this is of course possible e.g. when the microorganisms have been washed with water before the drying step) but may further include ingredients whose presence may be ascribed to the cultivation of the microorganisms and/or washing steps etc. What follows is that the "total mass of the microorganism" may further include (in addition to the microorganism) residual amount of storage buffer components/salts such as TRIS-based buffers, Saline based buffers etc. and/or residual amounts of the culture medium, growing medium, nutrient solutions, fermentation broths for example the fermentation broth that was used to culture the microorganisms etc., stabilizers, additives (e.g. drying additives) etc.

The present invention further provides in line with the findings of the present inventors a method for producing a microorganism with an increased NHase/Amidase activity ratio, comprising drying a NHase and Amidase producing microorganism as well as a method for producing a microorganism with a decreased Amidase activity, comprising drying a NHase and Amidase producing microorganism.

As explained above, a main goal that is achieved by the present invention is a bio-converted amide compound (bio-converted from a nitrile compound) with less or reduced acrylic acid as by-product, since acrylic acid is known to cause difficulties in a subsequent polymerization of the amide compound. Accordingly, this achievement is reflected by providing a method for reducing the formation of acrylic acid when producing an amide compound from a nitrile compound, comprising contacting acrylonitrile with a NHase and Amidase producing microorganism, wherein said microorganism is pre-treated by a drying step before being contacted with said nitrile compound. In particular, the inventors have found that by using a microorganism which has been pre-treated by a drying step before being contacted with the nitrile compound as described herein, the formation of acrylic acid may be reduced by at least 15%, preferably by at least 20%, more preferably by at least 25%, even more preferably by at least 30%, still more preferably by at least 40% and most preferably by at least 50% compared to a reference method.

The present inventors have further considered that bioconversion reactions, especially in industrial scale, should preferably be conducted in a rather simple way. In particular, in regard to the bio-conversion of a nitrile compound to an amide compound using a NHase comprising biocatalyst of the invention, the present inventors have considered that keeping the molar concentration of a buffer in the reaction mixture comparably low, preferably as low as possible, has several advantages for the bioconversion process. For example, if a comparably large amount of buffer is present in the reaction mixture, it would consequently be present in the wastewater in comparably large amounts. This means that the buffer will have to be removed from the wastewater again, which will result in additional technical efforts and costs. In addition, the presence of comparably large amounts of a buffer in the product, i.e. the amide solution, may negatively influence subsequent reaction steps, such as, for example, polymerization or copolymerization reactions. Hence, if a comparably large amount of buffer is added to the reaction mixture of the bioconversion, it will either have to be separated from the amide solution prior to further reaction steps, which will be accompanied by additional technical efforts and costs, or the buffer may result in a decrease of the quality of the product. Consequently, the bioconversion of a nitrile compound to an amide compound is preferably conducted in aqueous solution in the presence of comparably low amounts of buffer.

For the preparation of a reaction mixture for the bioconversion of a nitrile compound to an amide compound, a dried biocatalyst, which has been obtained by the methods of the present invention, for example, by spray drying or freeze drying, may in general be suspended in water, and said aqueous mixture containing the biocatalyst may be then transferred to the reactor in which the bioconversion is carried out and where the biocatalysts is contacted with an aqueous mixture and a nitrile compound that is to be converted into the corresponding amide. However, the present inventors have surprisingly found that, if a dried biocatalyst of the invention is mixed with a non-buffered aqueous solution, the pH of the aqueous mixture containing the biocatalyst will be in a weakly acidic range (e.g. pH 5 to 6.5). This is surprising since prior to drying, e.g. spray drying or freeze drying, the wet biocatalyst is in a medium that typically has a neutral pH (e.g. pH 6.7 to 7.5). Moreover, the reaction mixture during bioconversion is rather weakly basic. Without wishing to be bound by theory, it is believed that during the drying step, ammonia ($NH_3$) strips from the medium which results in the weakly acidic pH of the dried biocatalyst when mixed with an aqueous solution prior to bioconversion.

In this regard, the present inventors have surprisingly discovered that the acidic pH of the aqueous mixture of the dried biocatalyst results in a diminished activity of the NHase and that this diminishment may be irreversible, which means that the NHase activity will remain diminished even if the bioconversion is conducted in a reaction mixture that has a neutral or slightly basic pH.

The present inventors have conducted various experiments and have found out that if the dried biocatalyst is activated by suspending it in a buffered aqueous solution prior to bioconversion, wherein the solution has a neutral or slightly basic pH (e.g. pH 6.6 to 9), the biocatalyst will have a substantially increased NHase activity. This high NHase activity is maintained even if the activation mixture (i.e. the buffered aqueous mixture comprising the biocatalyst) is transferred to a non-buffered aqueous solution in order to give the reaction mixture. By this increased NHase activity the total reaction time of the bioconversion is crucially decreased as compared to the reaction time of the bioconversion where the same amount of biocatalyst has been suspended in water without buffer after spray drying. Moreover, simply adding the buffer to the reaction mixture does not lead to the same effect as when the dried biocatalyst has been re-suspended in the buffer as activation before adding to the reaction mixture. According to further experiments conducted by the present inventors, the biocatalyst also has a substantially increased NHase activity when the buffer is added to the cell suspension after fermentation and the biocatalyst is dried with the buffer and afterwards re-suspended in water or buffer.

As set out above, the activation of the biocatalyst may be performed by suspending the dried biocatalyst in an aqueous solution containing a buffer. Such activation can be performed on a small scale, i.e. the reaction volume required for the activation is comparably small. On the other hand, the reaction mixture in which the bioconversion of the nitrile compound to the amide compound is performed in general has a comparably large volume. Due to the low volume of the activation mixture compared to the volume of the reaction mixture, the buffer component is diluted in the reaction mixture when the activation mixture is transferred to the reactor for the bioconversion of the nitrile compound to the amide compound. Nevertheless, the beneficial effect of the buffer during the activation is preserved in the bioconversion. As said before, as a consequence of the enhanced NHase activity, the bioconversion of a nitrile compound to an amide compound using the biocatalyst exhibits a higher reaction rate if the same amount of biocatalyst is employed. Further, the amount of biocatalyst can be reduced while achieving a reaction rate that is even higher than the reaction rate when using a non-reduced amount of biocatalyst that has not undergone an activation step, i.e. a biocatalyst re-suspended in merely water after drying.

Thus, the present invention also relates to a method for producing an amide compound from a nitrile compound in aqueous mixture, the method comprising: (a) a pre-treatment of the biocatalyst by a drying step; (b) an activation step comprising mixing a dried biocatalyst of the invention with an aqueous solution to give an activation mixture, wherein the activation mixture comprises a buffer; and (c) converting the nitrile compound to the amide compound using the biocatalyst of the invention in a reaction mixture, wherein the reaction mixture comprises said buffer of step (b), and wherein the ratio of the molar concentration of the buffer in the activation mixture to the molar concentration of said buffer in the reaction mixture is about 2:1 or more. In particular, the ratio of the molar concentration of the buffer in the activation mixture to the molar concentration of said buffer in the reaction mixture is about 2:1 or more before the end of the conversion. It is not required in any one of the methods disclosed herein that the ratio is maintained constant during the conversion. Rather the ratio may vary during the conversion, as long as the ratio is about 2:1 or more. For example, the ratio may increase during the conversion. This may be the case if reactants are added to the reaction mixture during the conversion which dilute the reaction mixture and thereby decrease the buffer concentration in the reaction mixture. For example, the nitrile compound and/or water may be fed as reactants to the reaction mixture during the conversion. This increases the volume of the reaction mixture, and, thus, decreases the molar concentration of the buffer in the reaction mixture. As a result of the decrease of the molar concentration of the buffer in the reaction mixture, the ratio of the molar concentration of the buffer in the activation mixture to the molar concentration of the buffer in the reaction mixture increases. Thus, as can be seen from this example, the molar ratio can vary over the course of conversion reaction.

It is further envisaged that the ratio of the molar concentration of the buffer in the activation mixture to the molar concentration of said buffer in the reaction mixture may be about 3:1 or more, preferably about 4:1 or more, more preferably about 5:1 or more, even more preferably about 7:1 or more, still more preferably about 10:1 or more, still more preferably about 20:1 or more, still more preferably about 50:1 or more, most preferably about 100:1 or more. In particular, these ratios are present before the end of the conversion. Regarding the molar concentration of the buffer in the activation mixture and the molar concentration of the buffer in the reaction mixture, these concentrations are both indicated in mol/L (moles per liter). When calculating the ratio of the molar concentration of the buffer in the activation mixture and the molar concentration of the buffer in the reaction mixture, both the molar concentration of the buffer in the activation mixture and the molar concentration of the buffer in the reaction mixture have to be taken in mol/L. It is also contemplated by the invention, that the buffer of the activation mixture may be at least partially removed after the activation step and before the biocatalyst is contacted with a nitrile compound. As an illustrative example, this can be done by centrifugation of the activation mixture followed by discarding the supernatant, optionally followed by contacting the biocatalyst with another aqueous solution, or, as another illustrative example, by filtration. In such a case, the biocatalyst (suspension) will typically still contain residual buffer when the biocatalyst is contacted with the nitrile compound. It is understood by the skilled artisan, that the less residual buffer is present in the biocatalyst, the higher the ratio of the molar concentration of the buffer in the activation mixture to the molar concentration of said buffer in the reaction mixture may typically be.

The term "activation" as used herein in the context of a dried biocatalyst in general refers to mixing the dried biocatalyst with an aqueous solution to give an aqueous mixture comprising the biocatalyst and a buffer. Said mixture is also referred herein as "activation mixture". In accordance with any one of the methods described herein, the activation mixture may be prepared by mixing a buffer with an aqueous solution to give a buffered aqueous solution and subsequently dissolving or suspending the dried biocatalyst in the buffered aqueous solution. The activation mixture can also be prepared by mixing the dried biocatalyst with buffer components, in particular dry buffer components, and subsequently adding water to the mixture or adding the mixture to water, and dissolving the buffer components as well as dissolving or re-suspending the dried biocatalyst.

The term "reaction mixture" as used herein refers to an aqueous mixture comprising a biocatalyst and a nitrile compound and/or an amide compound. In some embodiments, the reaction mixture according to any one of the methods disclosed herein may be created by combining a biocatalyst that has undergone an activation step, an aqueous solution and a nitrile compound. Typically, the biocatalyst catalyzes the conversion of the nitrile compound to the amide compound in the reaction mixture. Thus, the term "reaction mixture" typically refers to a mixture including water, a biocatalyst, and a nitrile and/or an amide compound, at any time of a conversion process, including at the beginning of the reaction, when in an aqueous solution a biocatalyst is first contacted to a nitrile compound, as well as after the conversion has been stopped or ended but when the aqueous solution, the biocatalyst and an amide or nitrile compound are still present in the mixture.

The term "before the end of the conversion" as used herein refers to any time while a conversion of nitrile to amide in the reaction mixture is still ongoing. Typically it refers to any time, in which a reaction mixture is present and in which the conversion has not yet ended or stopped.

It is also contemplated in the methods disclosed herein that the buffer can be added to a biocatalyst suspension or solution before the biocatalyst is subjected to the drying step of the invention to give a dried biocatalyst. The biocatalyst may also be washed before the buffer is added. By adding the buffer prior to the drying step, the dried biocatalyst comprises the dried buffer components that have been added prior to the drying step. Thus, when contacting the dried biocatalyst comprising a buffer with an aqueous solution, the buffer components dissolve, which, together with the biocatalyst, gives an activation mixture. Further, it is also contemplated in the methods disclosed herein that the biocatalyst treated with buffer before the biocatalyst is subject of a drying step to give a dried biocatalyst which can subsequently be dissolved or resuspended in a buffer solution to give an activation mixture.

When the biocatalyst is activated with a buffer according to the methods disclosed herein, said activation does not require a long period of time. Preferably, said activation of the biocatalyst is carried out for about 1 minute or more, more preferably for about 5 minutes or more, even more preferably from about 10 minutes to about 10 hours, still more preferably from about 20 minutes to about 5 hours, most preferably from about 30 minutes to about 2 hours. When a dried biocatalyst is treated with a buffered aqueous solution to give the activation mixture, said activation mixture is typically directly used for the bioconversion, i.e. directly mixed with an aqueous solution and a nitrile compound to give the reaction mixture. On the other hand, if the biocatalyst is activated with a buffered solution or a buffer salt prior to the drying step, the dried biocatalyst can be subsequently stored for several months before bringing together said activated biocatalyst with an aqueous solution to give an activation mixture and to further mix said activation mixture with an aqueous solution and a nitrile compound to give the reaction mixture. As found out by the present inventors, said biocatalyst does not significantly lose activity during the storage period. This can be seen as a further advantage of said activation variants.

It is also contemplated by the methods disclosed herein that the buffer comprised in the activation mixture has a pKa in a range of from about 6 to about 9, preferably from about 6.5 to about 8. Here, the buffer may comprise a single component, or can be a mixture of more than one buffer component. It is also understood that one single component can have more than one pKa values. A buffer has typically a pKa in a range from about 6 to about 9 if it comprises a buffer component that has a pKa in the range from about 6 to about 9. For example, phosphate has three pKa values, 2.1, 7.2 and 12.7. Since one of the pKa values of phosphate is within the range of from about 6 to about 9, a buffer comprising phosphate may be understood as a buffer having a pKa in a range from about 6 to about 9.

It is also envisaged that the activation mixture has a pH value of from about 6.6 to about 9, preferably from about 6.6 to about 8.8, more preferably from about 6.7 to about 8.6, even more preferably from about 6.8 to about 8.4, still more preferably from about 6.9 to about 8.2, most preferably from about 7 to about 8.

Also contemplated by the invention is that different buffers are well suited to be used in the methods disclosed herein, i.e. to increase the NHase activity of a biocatalyst. It is envisaged that the buffer comprises an inorganic buffer or an organic buffer. It is further envisaged that the buffer may comprise a non-sulfonic acid buffer or a carboxylic acid buffer. Suitable buffers which may be used in the present invention may comprise a compound selected from the group consisting of phosphate, citrate, carbonate, 2-[(2-hydroxy-1,1-bis(hydroxymethy)ethyl)amino] ethanesulfonic acid (TES), 1,4-piperazinediethanesulfonic acid (PIPES), N-(2-acetamido)-2-aminoethanesulfonic acid (ACES), and tris(hydroxymethyl) aminomethane (TRIS), and any combination thereof. In particular, the buffer comprises a phosphate buffer or a citrate buffer or a combination thereof. Preferably, the buffer is a phosphate buffer.

It is further envisaged that the buffer is in a concentration in the activation mixture of about 10 mM to about 1 M, preferably about 20 mM to about 500 mM, more preferably about 50 mM to about 200 mM, even more preferably about 70 mM to about 130 mM, most preferably about 80 mM to about 120 mM.

It is further envisaged that the buffer concentration in the reaction mixture is about 100 mM or less, preferably about 50 mM or less, more preferably about 20 mM or less, even more preferably about 10 mM or less, still more preferably from about 5 mM to about 1 pM, still more preferably from about 4 mM to about 1 pM, still more preferably from about 3 mM to about 1 pM, still more preferably from about 2 mM to about 1 pM, still more preferably from about 1 mM to about 1 pM, still more preferably from about 0.8 mM to about 1 pM, still more preferably from about 0.5 mM to about 1 pM, still more preferably from about 0.4 mM to about 1 pM, still more preferably from about 0.3 mM to about 1 pM, still more preferably from about 0.2 mM to about 1 pM, most preferably from about 0.1 mM to about 1 pM.

It is also envisaged that the temperature of the activation is in the range of from about 0° C. to about 50° C., preferably from about 10° to about 40° C., more preferably from about 20° C. to about 37° C.

However, the present invention does not only encompass methods, it also encompasses the following uses.

Use of a NHase and Amidase producing microorganism as described herein for producing an amide compound from a nitrile compound.

Use of a drying method for increasing the NHase/Amidase activity ratio of a NHase and Amidase producing microorganism.

Use of a drying method for decreasing the Amidase activity of a NHase and Amidase producing microorganism.

The embodiments and definitions described herein in the context of the methods of the present invention are equally applicable to the uses of the present invention, mutatis mutandis.

In another aspect, the present invention provides an aqueous amide compound solution obtained by the methods of the present invention. Such an aqueous amide compound solution is preferably characterized by a reduced acrylic acid content in comparison to an aqueous amide compound solution obtained from the same organism which, however, is not pre-treated by a drying step before being contacted with a nitrile compound. In particular, the concentration of acrylic acid of such an aqueous amide compound solution is 1500 ppm or less, preferably 1200 ppm or less, more preferably 1000 ppm or less, further preferably 750 ppm or less, even more preferably 500 ppm or less, still more preferably 300 ppm or less, still more preferably 200 ppm or less and most preferably 100 ppm or less, wherein indications of ppm each relate to weight parts and are each referred to the total weight of the aqueous amide compound solution.

Furthermore, the present invention provides a composition comprising acrylamide or polyacrylamide and a NHase and Amidase producing microorganism, said microorganism exhibiting a NHase/Amidase activity ratio of at least 400 Units and/or a and/or a ratio of the NHase activity to Amidase activity which is increased by a factor of at least 1.7, when compared to a reference microorganism.

Unless otherwise required by context, singular terms shall include pluralities and plural terms shall include the singular. As used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

As described herein, "preferred embodiment" or "preferred aspect" means "preferred embodiment of the present invention" or "preferred aspect of the present invention". Likewise, as described herein, "an embodiments", "another embodiment", "an aspect", "another aspect" means "an embodiments of the present invention", "another embodiment of the present invention", "an aspect of the present invention" and "another aspect of the present invention", respectively.

Unless otherwise defined herein, scientific and technical terms used in connection with the present invention shall have the meanings that are commonly understood by those of ordinary skill in the art. The methods and techniques of the present invention are generally performed according to conventional methods well known in the art. Those skilled in the art will recognize, or be able to ascertain, using not more than routine experimentation, many equivalents to the specific embodiments of the invention described herein. Such equivalents are intended to be encompassed by the present invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

EXAMPLES

Figure 1:
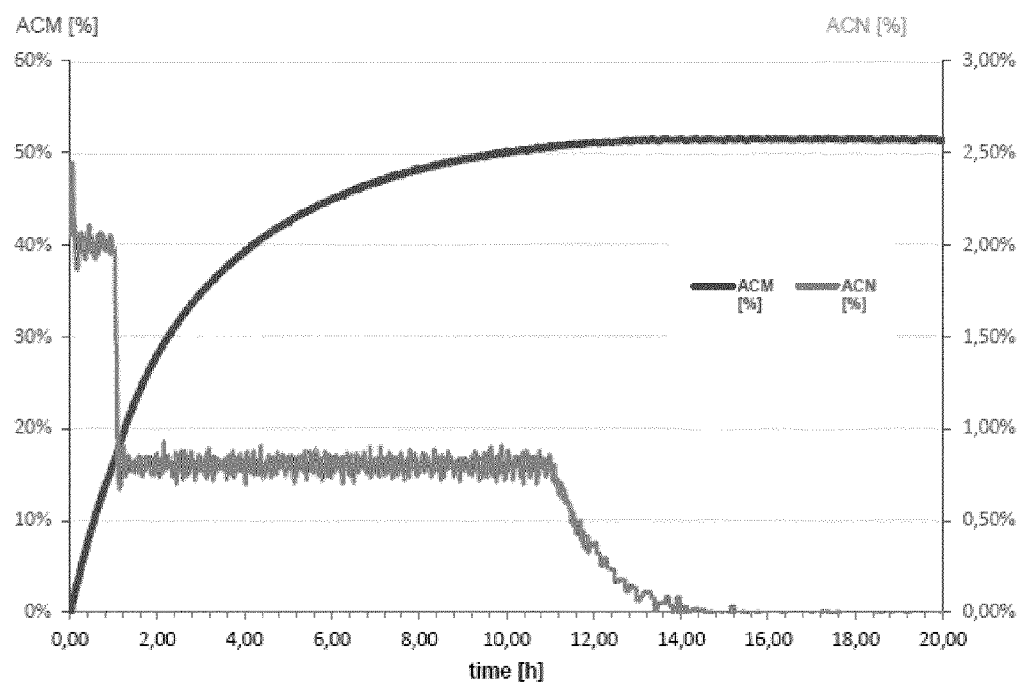
FIG. 1: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in water after spray drying. A total amount of 3.36 g of the dried biocatalyst (batch Ch10) was employed, which had an NHase activity of 116 kU/g as measured before the beginning of the bioconversion. The reaction was conducted at a 4 L scale (L=liter) at 26° C. At the beginning of the reaction, re-suspended biocatalyst corresponding to 2.4 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.96 g dried biocatalyst was added to the reactor. After 1 h after beginning of the bioconversion, the ACN concentration was maintained at 0.8 w/w %, until a total amount of 1553 g acrylonitrile has been added to the reactor. Total reaction time until full conversion (<100 ppm residual ACN) was 13.78 h.

The following examples further describe and exemplify the invention provided herein without limiting the invention to any specifications or embodiments defined therein.

Three experiments in connection with the production of an amide compound from a nitrile compound were conducted. The inoculum for production was either fermentation broth containing a biocatalyst, a concentrate of said biocatalyst, a spray-dried biocatalyst or a freeze-dried biocatalyst. The concentrate is the form of the biocatalyst prior to its pre-treating by a drying step before being contacted with said nitrile compound to be converted to an amide compound. Concentrate means that the fermentation broth is concentrated by reducing liquid fermentation broth, e.g. by centrifugation. Thus, the fermentation broth, the concentrate and the dried powder as used in this Example contain the same biocatalyst. The activity ratio between NHase and Amidase as well as the NHase activity were determined in line with commonly known procedures. NHase activity in the setting up means that all setting ups contain the same amount of biocatalyst as is reflected by the almost identical NHase activity. Hence, the conditions were the same for the fermentation broth, concentrate and dried powder. In addition, the concentration of acrylic acid was determined. These data are summarized in Table 1, below, as well as the end of the bio-conversion reaction.

Exp 1: Water and 20 g of ACN were placed in a reactor. The amount of water was adjusted so that the total amount of water+biocatalyst was 2447 g. Three different forms of a biocatalyst were used in independent runs:
(i) a fermentation broth containing *Rhodococcus rhodochrous* NCIMB 41164. Water content: 88.2% (w/w).
(ii) a concentrate, for which the fermentation broth from (i) has been concentrated by centrifugation. Water content: 83.5% (w/w).
(iii) dry powder obtained by spray drying of the concentrate from (ii). Residual water content of the dry powder: 8.05% (w/w). Spray drying was operated at 115° C. gas inlet temperature and 65° C. gas outlet temperature.

The biocatalyst was added to the reactor, whereby the reaction started. During the reaction, 1533 g of additional acrylonitrile was added so that the overall reaction batch size at the end was 4000 g. The temperature was kept constant at 26° C. during the reaction. The ACN concentration was measured by on-line FTIR, and the rate of addition of ACN was adjusted so that the ACN concentration in the reaction mixture was kept constant at 0.8±0.1% (w/w) until the entire ACN has been added to the reaction. The reaction was stopped after ACN concentration had decreased to <100 ppm due to conversion. At the end of the reaction, the acrylamide (ACM)-concentration in every run was 51% (w/w).

Exp 2: Water and 60 g of ACN were placed in a reactor. The amount of water was adjusted so that the total amount of water+biocatalyst was 2447 g. Three different forms of a biocatalyst were used in independent runs:
(i) a fermentation broth containing *Rhodococcus rhodochrous* NCIMB 41164. Water content: 91.8% (w/w).
(ii) a concentrate, for which the fermentation broth of (i) has been concentrated by centrifugation. Water content: 85.3% (w/w).
(iii) dry powder obtained by spray drying of the concentrate from (ii). Residual water content of the dry powder: 6.8% (w/w). Spray drying was operated at 115° C. gas inlet temperature and 60° C. gas outlet temperature.

The biocatalyst was added to the reactor, whereby the reaction started. During the reaction, 1493 g of additional acrylonitrile was added so that the overall reaction batch size at the end was 4000 g. The temperature was kept constant at 26° C. during the reaction. The ACN concentration was measured by on-line FTIR, and the rate of addition of ACN was adjusted so that ACN concentration in the reaction mixture was controlled. During the first hour of the reaction, ACN concentration was kept constant at 2.0%±0.15% (w/w), thereafter, it was kept constant at 0.8%±0.15% (w/w) until the entire ACN has been added to the reaction. The reaction was stopped after ACN concentration had decreased to <100 ppm due to conversion. At the end of the reaction, the ACM-concentration in every run was 50% (w/w).

Exp 3: Water and 60 g of ACN were placed in a reactor. The amount of water was adjusted so that the total amount of water+biocatalyst was 2447 g. Two different forms of a biocatalyst were used in independent runs:
(i) a concentrate, for which a fermentation broth containing *Rhodococcus rhodochrous* NCIMB 41164 has been concentrated by centrifugation. Water content: 81% (w/w).
(ii) dry powder obtained by freeze drying of the concentrate from (i). Residual water content of the dry powder: 6.8% (w/w).

The biocatalyst was added to the reactor, whereby the reaction started. During the reaction, 1493 g of additional acrylonitrile was added so that the overall reaction batch size at the end was 4000 g. The temperature was kept constant at 26° C. during the reaction. The ACN concentration was measured by on-line FTIR, and the rate of addition of ACN was adjusted so that the ACN concentration in the reaction mixture was controlled. During the first hour of reaction, ACN concentration was kept constant at 2.0%±0.15% (w/w), thereafter, it was kept constant at 0.8%±0.15% (w/w) until the entire ACN has been added to the reaction. The reaction was stopped after ACN concentration had decreased to <100 ppm due to conversion. At the end of the reaction, the ACM-concentration in every run was 50% (w/w).

TABLE 1

| No. | Form of biocatalyst | Activity ratio NHase/Amidase | NHase activity in the setting up [kU] | End of reaction [h] | Acrylic acid [ppm] |
|---|---|---|---|---|---|
| Exp. 1 | fermentation broth | 209 | 220 | 4.9 | 844 |
|  | concentrate | 96 | 227 | 4.5 | 758 |
|  | spray-dried powder | 330 | 220 | 5.47 | 260 |
| Exp. 2 | fermentation broth | 108 | 247 | 4.9 | 849 |
|  | concentrate | 81 | 247 | 6.4 | 856 |
|  | spray-dried powder | 418 | 246 | 7.5 | 281 |
|  | spray-dried powder | 418 | 270 | 5.9 | 258 |
| Exp. 3 | concentrate | N/A | 247 | 5.22 | 516 |
|  | Freeze-dried powder | N/A | 247 | 5.35 | 297 |

It is apparent that a microorganism which was pre-treated by a drying step before being contacted with a nitrile compound which is then subject to bio-conversion by said microorganism has the highest value as regards NHase/Amidase activity. Given the fact that in each reaction (setting up) almost the same amount of biocatalyst was used (as determined by the NHase activity of each of the employed biocatalyst forms, namely fermentation/concentrate/spray-dries/freeze-dried), it is apparent that the drying step, i.e. subjecting a biocatalyst to a drying step before bringing it into contact with a nitrile compound significantly influences the amount of the by-product acrylic acid. This means that because of the drying step, the Amidase activity is reduced to such an extent that such dried microorganisms produce an amide compound with less acrylic acid as by-product which is apparent from the outermost right column. In sum, since reaction parameters are kept equal between the different setting ups, it is apparent that the improvement in reducing the amount of acrylic acid can be ascribed to the drying step.

Exp 4: Freeze dried powder was obtained by lyophilisation of the concentrated fermentation broth in a Christ Alpha 2-4 LSCplus laboratory freeze dryer. The concentrate was first frozen overnight at −20° C. and subsequently dried. During drying, the shelf temperature was −25° C., the condensator temperature was −82° C. and the chamber pressure was 0.25 mbar.

Water and 18 g of ACN were placed in a reactor. The amount of water was adjusted so that the total amount of water+biocatalyst was 1835 g. Two different forms of a biocatalyst were used in independent runs:
(i) a fermentation broth containing *Rhodococcus rhodochrous* J1. Water content: 96.1% (w/w).
(ii) a dry powder obtained by concentration of (i) by centrifugation up to a water content of 83.6% (w/w) and freeze drying of the concentrate.

The biocatalyst was added to the reactor, whereby the reaction started. During the reaction, 1147 g of additional acrylonitrile was added so that the overall reaction batch size at the end was 3000 g. The temperature was kept constant at 23° C. during the reaction. The ACN concentration was measured by on-line FTIR, and the rate of addition of ACN was adjusted so that the ACN concentration in the reaction mixture was kept constant at 1.0±0.1% (w/w) until the entire ACN had been added to the reaction. The reaction was stopped after ACN concentration had decreased to <100 ppm due to conversion. At the end of the reaction, the ACM concentration in every run was 51% (w/w).

Exp 5: The experiments were performed as in Exp 4 above, except that the ACN concentration in the reaction mixture was controlled at 0.3±0.1% (w/w) during the reaction.

The results from Exp 4-5 are shown in table 2 below.

TABLE 2

| No. | Form of biocatalyst | Activity ratio NHase/ Amidase | NHase activity loading [kU/kg batch size] | End of reaction [h] | Acrylic acid [ppm] |
|---|---|---|---|---|---|
| Exp. 4 | Fermentation broth | 138 | 64.8 | 5.7 | 604 |
| | Concentrate | 112 | | Not performed | |
| | Freeze-dried powder | 211 | 62.3 | 5.0 | 305 |
| Exp. 5 | Fermentation broth | 138 | 64.8 | 7.5 | 885 |
| | Concentrate | 112 | | Not performed | |
| | Freeze-dried powder | 211 | 62.3 | 6.6 | 568 |

Exp. 6: Activation of a spray dried biocatalyst

Spray dried biocatalyst is weighed out in a centrifuge tube (Falcon®) and suspended in 30 ml buffer for the activation step as disclosed herein. Unless indicated otherwise, said buffer was 100 mM phosphate buffer, pH 7.0. The biocatalyst is buffer-treated for 0.5 h at room temperature. Then the biomass (biocatalyst) suspension is transferred to the reactor and further incubated for 1 h. After addition of the biomass suspension to the reactor, the centrifuge tube is rinsed with water and the solvent is transferred as well to the reactor. This amount of water is considered for the water weighing into the reactor.

Exp. 7: General protocol for bioconversion

The hydration of acrylonitrile is generally carried out in a stirred tank reactor (rpm=250, volume V=4 L) with an external circulating loop for cooling. For this purpose 2.4 L of water is filled in the reactor as well as the biocatalyst. Biomass is added as spray dried cells of *Rhodococcus rhodochrous*, which has been previously suspended into water. As described herein, the spray dried cells can also directly be suspended in buffer according to the activation step disclosed herein. In order to start the reaction, acrylonitrile is dosed into the stirred tank reactor employing a process control system. A constant concentration of acrylonitrile of 0.5 to 5 w/w % is adjusted by the use of an online Fourier Transform Infrared (FTIR) analysis, which directly communicates with the process control unit (Labview). The reaction temperature is constantly kept at 20 to 29° C. The dosage of acrylonitrile is stopped after the addition of 1553 g acrylonitrile. After the complete conversion of residual acrylonitrile, i.e. when a residual ACN concentration of <100 ppm is reached, and obtaining 52 w/w % acrylamide, the reaction is finished.

Exp. 8: Determination of the concentration of acrylic acid, acrylamide, acrylic acid and acrylonitrile in the obtained aqueous acrylamide solutions by HPLC The following conditions were applied in order to determine the contents of acrylamide, acrylic acid and acrylonitrile:

Column: Aqua C18, 250*4.6 mm (Phenomenex)
Guard column: C18 Aqua
Temperature: 40° C.
Flow rate: 1.00 ml/min
Injection volume: 1.0 μl
Detection: UV detector, wavelength 210 nm
Stop time: 8.0 minutes
Post time: 0.0 minutes
Maximum pressure: 250 bar
Eluent A: 10 mM $KH_2PO_4$, pH 2.5
Eluent B: Acetonitrile

| Gradient: | | | |
|---|---|---|---|
| Time [min] | A [%] | B [%] | Flow [ml/min] |
| 0.0 | 90.0 | 10.0 | 1.00 |
| 8.0 | 90.0 | 10.0 | 1.00 |

Matrix: Fermentation broths, bioconversion mixtures
Sample is filtered through 0.22 μm

| Analytes: | |
|---|---|
| | Retention time [min] |
| Acrylamide | 3.29 |
| Acrylic acid | 3.91 |
| Acrylonitrile | 4.35 |

Exp 9

Spray dried *Rhodococcus rhodochrous* (NCIMB 41164) of batch Ch10 was used for bioconversion reactions of acrylonitrile to acrylamide. The bioconversion reactions were carried out according to the protocol of Exp 7.

Figure 2:
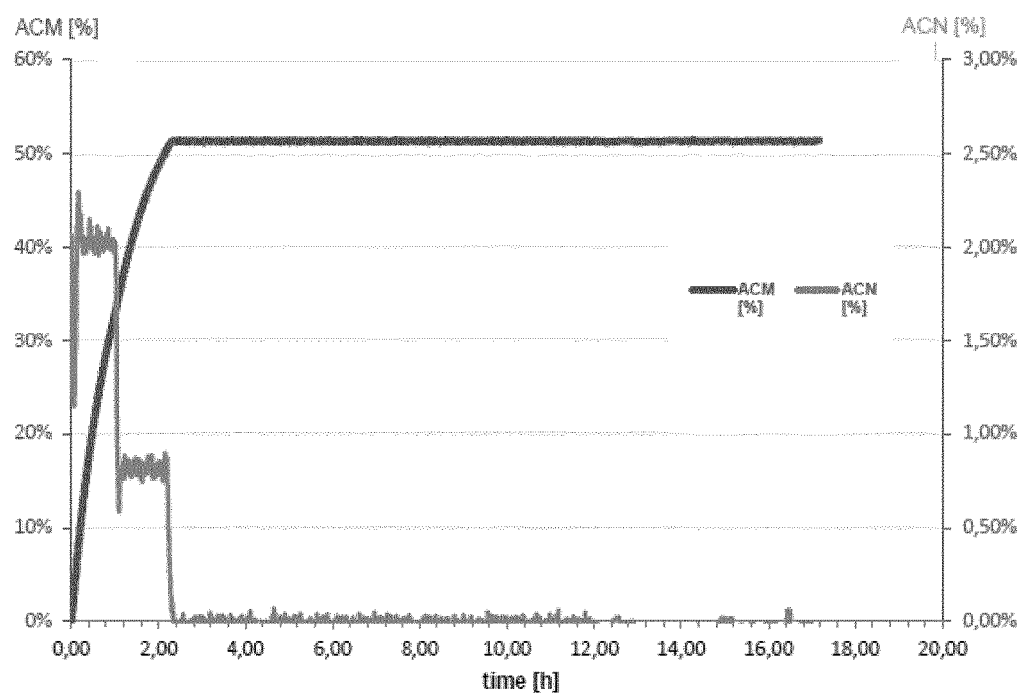
FIG. 2: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in 33 mL of 100 mM phosphate buffer (pH 7.0) after spray drying, which corresponds to the activation step as disclosed herein. The activation step was conducted for 1.0 h. A total amount of 3.36 g of the dried biocatalyst (batch Ch10) was employed, which had an NHase activity of 116 kU/g as measured before the beginning of the bioconversion. The reaction was conducted at a 4 L scale (L=liter) at 26° C. At the beginning of the reaction, re-suspended biocatalyst corresponding to 2.4 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.96 g dried biocatalyst was added to the reactor. After 1 h after beginning of the bioconversion, the ACN concentration was maintained at 0.8% w/w, until a total amount of 1553 g acrylonitrile has been added to the reactor. Total reaction time until full conversion (<100 ppm residual ACN) was 2.31 h.
Figure 3:
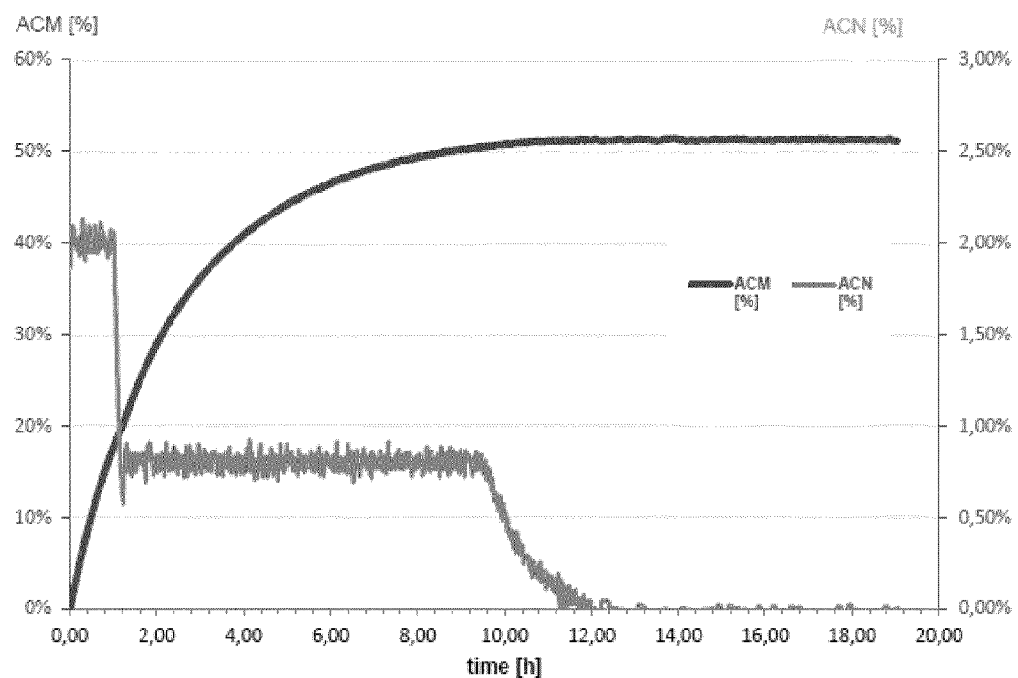
FIG. 3: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in water after spray drying. A total amount of 3.36 g of the dried biocatalyst (batch Ch10) was employed, which had an NHase activity of 116 kU/g as measured before the beginning of the bioconversion. The reaction was conducted at a 4 L scale (L=liter) at 26° C. Directly prior to biocatalyst addition, 33 mL of 100 mM phosphate buffer (pH 7.0) was added to the reactor, which corresponds to the amount of buffer that was used in the activation step of the experiment depicted in FIG. 2. At the beginning of the reaction, re-suspended biocatalyst corresponding to 2.4 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.96 g dried biocatalyst was added to the reactor. After 1 h after beginning of the bioconversion, the ACN concentration was maintained at 0.8 w/w %, until a total amount of 1553 g acrylonitrile has been added to the reactor. Total reaction time until full conversion (<100 ppm residual ACN) was 11.98 h.
Figure 4:
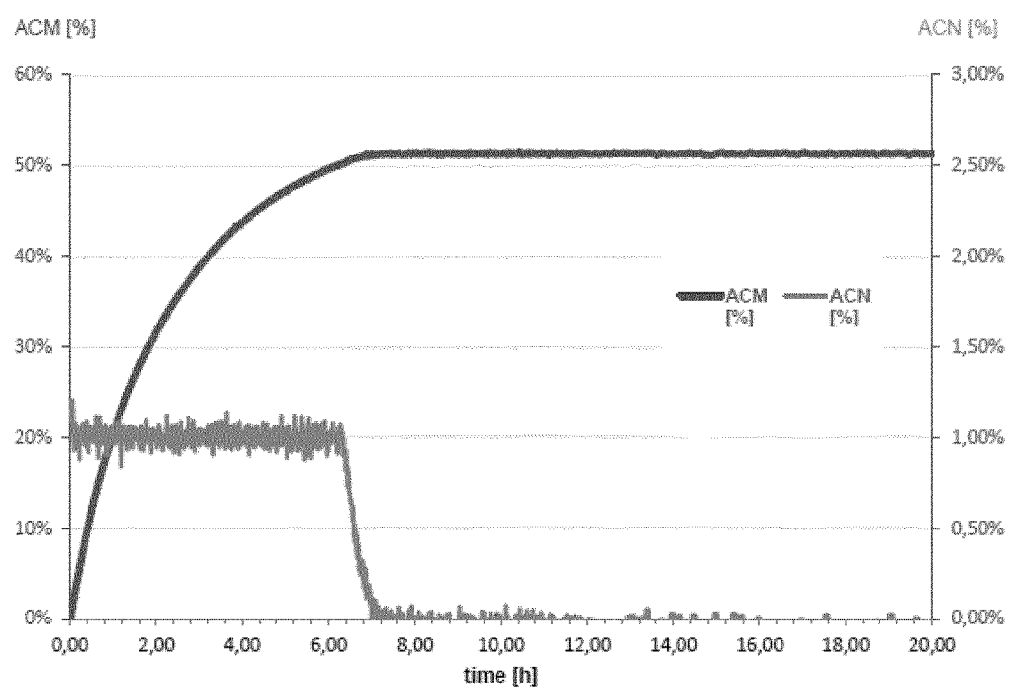
FIG. 4: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in 30 mL of 100 mM phosphate buffer (pH 7.0), which corresponds to the activation step disclosed herein. The activation step was conducted for 0.5 h. 1.8 g of the dried biocatalyst (batch Ch10) was employed, which had an NHase activity 116 kU/g as measured before the beginning of the bioconversion. The reaction was conducted at a 4 L scale (L=liter) at 23° C. At the beginning of the reaction, re-suspended biocatalyst corresponding to 1.8 g dried biocatalyst was added to the reactor. The ACN concentration after beginning of the bioconversion was maintained at 1 w/w % by feeding ACN to the reactor, until a total amount of 1553 g acrylonitrile has been added to the reactor. Total reaction time until full conversion (<100 ppm residual ACN) was 7.13 h.

In Run 1 (depicted in FIG. 1), 3.36 g biocatalyst that has been resuspended in water was used (2.4 g biocatalyst was added at the beginning of the bioconversion, 0.96 g biocatalyst was added after 1 h). In Run 2 (depicted in FIG. 2), 3.36 g biocatalyst was used (2.4 g biocatalyst was added at the beginning of the bioconversion, 0.96 g biocatalyst was added after 1 h) that has been activated with 100 mM phosphate buffer (pH 7.0), according to the invention. Activation was conducted according to Exp. 6. In Run 3 (depicted in FIG. 3), 3.36 g biocatalyst that has been resuspended in water was used (2.4 g biocatalyst was added at the beginning of the bioconversion, 0.96 g biocatalyst was added after 1 h), but the same amount of phosphate buffer that has been used in the activation step of Run 2 was directly added to the reactor prior to the addition of the biocatalyst. In Run 4 (depicted in FIG. 4), 1.8 g biocatalyst was used (1.8 g biocatalyst was added at the beginning of the bioconversion) that has been buffer-treated with 100 mM phosphate buffer (pH 7.0) according to Exp. 6. The results are outlined in the table below.

| Run # | Biocatalyst | Activation | Total reaction time |
|---|---|---|---|
| 1 | 3.36 g *Rhodococcus rhodochrous* (NCIMB 41164) of batch Ch10 | no/resuspension in water | 13.78 h |
| 2 | 3.36 g *Rhodococcus rhodochrous* (NCIMB 41164) of batch Ch10 | 100 mM phosphate buffer (pH 7.0) | 2.31 h |
| 3 | 3.36 g *Rhodococcus rhodochrous* (NCIMB 41164) of batch Ch10 | no/resuspension in water addition of 33 mL phosphate buffer (100 mM, pH 7.0) to the reactor | 11.98 h |
| 4 | 1.8 g *Rhodococcus rhodochrous* (NCIMB 41164) of batch Ch10 | 100 mM phosphate buffer (pH 7.0) | 7.13 h |

As can be seen from Run 2 (FIG. 2), activation of the dried biocatalyst using phosphate buffer reduces the total reaction time from 13.78 h (Run 1, FIG. 1) to 2.31 h. Run 3 (FIG. 3) shows that addition of phosphate buffer to the reaction mixture without activation of the dried biocatalyst has almost no influence on the reaction time compared to Run 1. Run 4 (FIG. 4) demonstrates that if the dried biocatalyst is activated using phosphate buffer, the amount of the biocatalyst can be reduced from 3.36 g to 1.8 g while the total reaction time is still less than using 3.36 g of non-buffer-treated biocatalyst as in Run 1.

Exp 10:

Spray dried *Rhodococcus rhodochrous* (NCIMB 41164) of batch V3 was used for bioconversion reactions of acrylonitrile to acrylamide. The bioconversion reactions were carried out according to the protocol of Exp 7.

Figure 5:
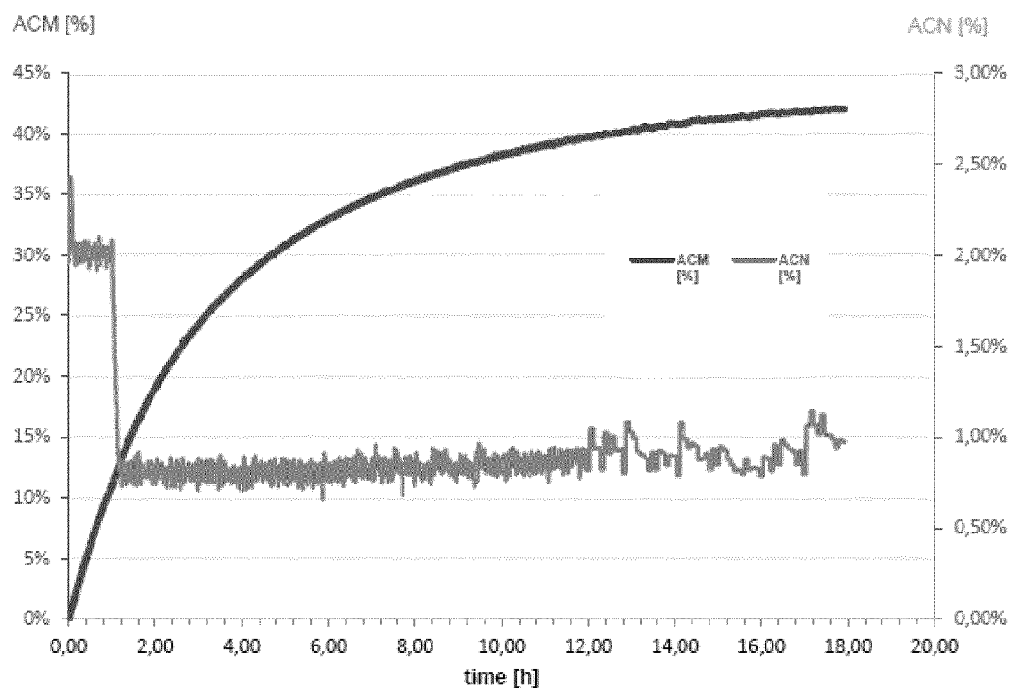
FIG. 5: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in water. A total amount of 1.29 g of the dried biocatalyst (batch V3) was employed, which had an NHase activity 172 kU/g as measured before the beginning of the bioconversion. The reaction was conducted at a 4 L scale (L=liter) at 26° C. At the beginning of the reaction, re-suspended biocatalyst corresponding to 0.92 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.37 g dried biocatalyst was added to the reactor. After 1 h after beginning of the bioconversion, the ACN concentration was maintained at 0.8 w/w %, until a total amount of 1553 g acrylonitrile has been added to the reactor. No full conversion (<100 ppm residual ACN) was reached after 20 h.
Figure 6:
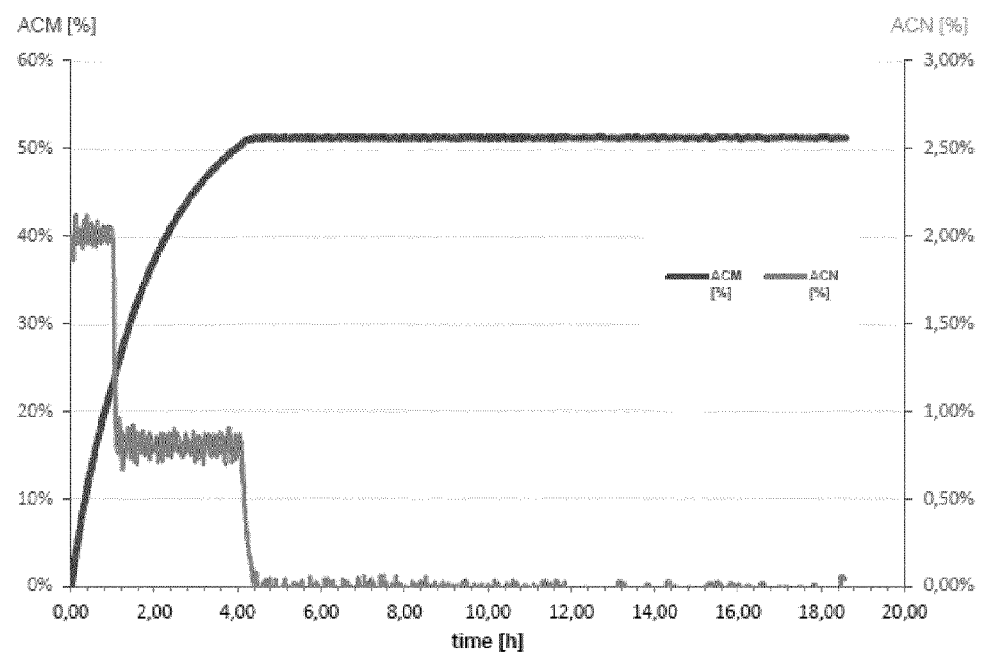
FIG. 6: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in 30 mL of 100 mM phosphate buffer (pH 8.0), which corresponds to the activation step. The activation step was conducted for 0.5 h. A total amount of 1.29 g of the dried biocatalyst (batch V3) was employed, which had an NHase activity 172 kU/g as measured before the beginning of the bioconversion. The reaction was conducted at a 4 L scale (L=liter) at 26° C. At the beginning of the reaction, re-suspended biocatalyst corresponding to 0.92 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.37 g dried biocatalyst was added to the reactor. After 1 h after beginning of the bioconversion, the ACN concentration was maintained at 0.8 w/w %, until a total amount of 1553 g acrylonitrile has been added to the reactor. Total reaction time until full conversion (<100 ppm residual ACN) was 4.4 h.
Figure 7:
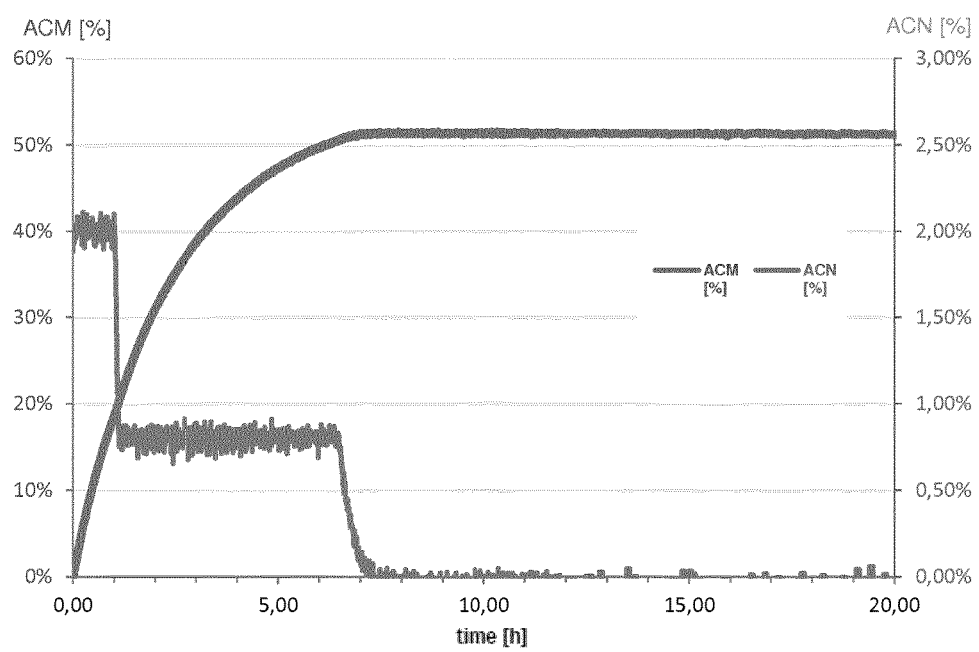
FIG. 7: Time course of acrylamide (ACM, depicted in dark grey) [%] and acrylonitrile (ACN, depicted in light grey) [%] concentrations in w/w % in a bioconversion of acrylonitrile to acrylamide applying spray dried *Rhodococcus rhodochrous* NCIMB 41164 as biocatalyst. The dried biocatalyst has been re-suspended in 30 mL of 100 mM citrate buffer (pH 7.0), which corresponds to the activation step. The activation step was conducted for 0.5 h. A total amount of 1.29 g of the dried biocatalyst (batch V3) was employed, which had an NHase activity 172 kU/g as measured before the beginning of the bioconversion. The reaction was conducted at a 4 L scale (L=liter) at 26° C. At the beginning of the reaction, re-suspended biocatalyst corresponding to 0.92 g dried biocatalyst was added to the reactor. The ACN concentration from 0 h to 1 h after beginning of the bioconversion was maintained at 2 w/w % by feeding ACN to the reactor. At 1 h after beginning of the bioconversion, re-suspended biocatalyst corresponding to 0.37 g dried biocatalyst was added to the reactor. After 1 h after beginning of the bioconversion, the ACN concentration was maintained at 0.8 w/w %, until a total amount of 1553 g acrylonitrile has been added to the reactor. Total reaction time until full conversion (<100 ppm residual ACN) was 7.25 h.

In Run 5 (depicted in FIG. 5), 1.29 g biocatalyst that has been resuspended in water was used (0.92 g biocatalyst was added at the beginning of the bioconversion, 0.37 g biocatalyst was added after 1 h). In Run 6 (depicted in FIG. 6), 1.29 g biocatalyst was used (0.92 g biocatalyst was added at the beginning of the bioconversion, 0.37 g biocatalyst was added after 1 h) that has been activated with 100 mM phosphate buffer (pH 8.0) as disclosed herein. Activation was conducted according to Exp. 6. In Run 7 (depicted in FIG. 7), 1.29 g biocatalyst was used (0.92 g biocatalyst was added at the beginning of the bioconversion, 0.37 g biocatalyst was added after 1 h) that has been activated with 100 mM citrate buffer (pH 7.0). The results are outlined in the table below.

| Run # | Biocatalyst | Activation | Total reaction time |
|---|---|---|---|
| 5 | 1.29 g *Rhodococcus rhodochrous* (NCIMB 41164) of batch V3 | no/resuspension in water | Incomplete conversion after 20 h |
| 6 | 1.29 g *Rhodococcus rhodochrous* (NCIMB 41164) of batch V3 | 100 mM phosphate buffer (pH 8.0) | 4.39 h |
| 7 | 1.29 g *Rhodococcus rhodochrous* (NCIMB 41164) of batch V3 | 100 mM citrate buffer (pH 7.0) | 7.25 h |

As can be seen from Runs 6 and 7 (FIGS. 6 and 7), both the activation step of *Rhodococcus rhodochrous* (NCIMB 41164) of batch V3 with phosphate buffer (100 mM, pH 8.0) and citrate buffer (100 mM, pH 7.0) leads to a dramatic reduction of total reaction time from an incomplete conversion after 20 h to a complete conversion after 4.39 h and 7.25 h, respectively.

The invention claimed is:

1. A method for producing an amide compound from a nitrile compound, the method comprising:
   contacting the nitrile compound with a microorganism producing a nitrile hydratase (NHase) and an amidase, wherein the microorganism has been previously pre-treated by drying before the contacting with the nitrile compound, wherein a ratio of a NHase activity to an amidase activity of the microorganism is increased, when compared to a reference microorganism, which is not pre-treated by drying before being contacted with the nitrile compound,
   wherein the microorganism is selected from the group consisting of *Rhodococcus rhodochrous*, *Rhodococcus pyridinovorans*, *Rhodococcus erythropolis*, *Rhodococcus equi*, *Rhodococcus ruber*, and *Rhodococcus opacus*,
   the amide compound is at least one selected from the group consisting of acrylamide, methacrylamide, acetamide, and nicotinamide,
   the nitrile compound is at least one selected from the group consisting of acrylonitrile, methacrylonitrile, acetonitrile, and 3-cyanopyridine, and
   wherein the drying has been conducted by spray drying, freeze-drying, heat drying, air drying, vacuum drying, fluidized-bed drying, spray granulation, or a combination thereof.

2. The method of claim 1, wherein the ratio of the NHase activity to the amidase activity of the microorganism is increased by a factor of at least 1.4, when compared to the reference microorganism.

3. The method of claim 1, wherein the ratio of the amidase activity to the NHase activity of the microorganism is decreased by a factor of at least 0.7, when compared to the reference microorganism, and wherein the reference microorganism is the microorganism producing a nitrile hydratase (NHase) and an amidase that has not been pre-treated by drying.

4. The method of claim 1, wherein the microorganism exhibits an NHase/amidase activity ratio of at least 400.

5. A method for producing an amide compound from a nitrile compound, the method comprising:
   a) drying a microorganism producing a NHase and an amidase; and
   b) contacting the nitrile compound with the microorganism after drying
   wherein drying increases a NHase/amidase activity ratio of the microorganism, compared to a reference microorganism, which is not treated by drying, wherein the microorganism is selected from the group consisting of *Rhodococcus rhodochrous*, *Rhodococcus pyridinovorans*, *Rhodococcus erythropolis*, *Rhodococcus equi*, *Rhodococcus ruber*, and *Rhodococcus opacus*,
   the amide compound is at least one selected from the group consisting of acrylamide, methacrylamide, acetamide, and nicotinamide,
   the nitrile compound is at least one selected from the group consisting of acrylonitrile, methacrylonitrile acetonitrile, and 3-cyanopyridine, and
   wherein the drying has been conducted by spray drying, freeze-drying, heat drying, air drying, vacuum drying, fluidized-bed drying, spray granulation, or a combination thereof.

6. The method of claim 1, further comprising reconstituting the pre-treated microorganism after the drying, wherein the contacting is conducted with a reconstituted microorganism.

7. The method of claim 6, wherein in the reconstituting, the pre-treated microorganism is suspended in an aqueous composition.

8. The method of claim 1, wherein the contacting is conducted with the pre-treated microorganism in the form of a powder, granule, or suspension, and/or in the form of a matrix bound microorganism.

9. The method of claim 1, wherein the microorganism is *Rhodococcus rhodochrous* or *Rhodococcus pyridinovorans*.

10. The method of claim 9, wherein the microorganism is *Rhodococcus rhodochrous* (NCIMB 41164), *Rhodococcus rhodochrous* (FERM BP-1478) or *Rhodococcus rhodochrous* M33.

11. The method of claim 1, wherein the nitrile compound is acrylonitrile.

12. The method of claim 1, wherein the amide compound is acrylamide.

13. The method of claim 1, further comprising:
   activating by mixing the dried microorganism with an aqueous solution to obtain an activation mixture, wherein the activation mixture comprises a buffer, and
   converting the nitrile compound to the amide compound by contacting the nitrile compound with the activation mixture in a reaction mixture, wherein the reaction mixture comprises the buffer and wherein a ratio of a molar concentration of the buffer in the activation mixture to a molar concentration of the buffer in the reaction mixture is about 2:1 or more.

14. A method for producing a microorganism with an increased NHase/amidase activity ratio, comprising:
   drying a microorganism producing a NHase and an amidase, and contacting a nitrile compound with the microorganism after the step of drying,
   wherein the microorganism is selected from the group consisting of *Rhodococcus rhodochrous*, *Rhodococcus pyridinovorans*, *Rhodococcus erythropolis*, *Rhodococcus equi*, *Rhodococcus ruber*, and *Rhodococcus opacus*,
   and the drying is conducted by spray drying, freeze-drying, heat drying, air drying, vacuum drying, fluidized-bed drying, spray granulation, or a combination thereof.

15. A method for reducing the formation of acrylic acid when producing acrylamide from an acrylnitrile compound, the method comprising contacting acrylonitrile with a microorganism producing a NHase and an amidase obtained by the method of claim 14.

16. The method of claim 1, wherein the microorganism producing a NHase and an amidase is not immobilized before being dried.

17. The amide compound obtained by the method of claim 1, wherein the amide compound is in an aqueous solution.

18. A composition comprising acrylamide or polyacrylamide and a microorganism producing a NHase and an amidase that has been pre-treated by drying, wherein the microorganism exhibits a NHase/amidase activity ratio of at least 400, and/or wherein a ratio of a NHase activity to an amidase activity is increased by a factor of at least 1.7, when compared to a reference microorganism, which is the same microorganism but has not been pretreated by drying, wherein the microorganism is selected from the group consisting of *Rhodococcus rhodochrous*, *Rhodococcus pyridinovorans*, *Rhodococcus erythropolis*, *Rhodococcus equi*, *Rhodococcus ruber*, and *Rhodococcus opacus*, and wherein the drying has been conducted by spray drying, freeze-drying, heat drying, air drying, vacuum drying, fluidized-bed drying, spray granulation, or a combination thereof.

* * * * *

SEQUENCE LISTING

<160> NUMBER OF SEQ ID NOS: 4

<210> SEQ ID NO 1
<211> LENGTH: 612
<212> TYPE: DNA
<213> ORGANISM: Rhodococcus rhodochrous
<220> FEATURE:
<223> OTHER INFORMATION: alpha-subunit of nitrile hydratase of
      Rhodococcus rhodochrous

<400> SEQUENCE: 1

```
gtgagcgagc acgtcaataa gtacacggag tacgaggcac gtaccaaggc gatcgaaacc      60
ttgctgtacg agcgagggct catcacgccc gccgcggtcg accgagtcgt ttcgtactac     120
gagaacgaga tcgcccgat gggcggtgcc aaggtcgtgg ccaagtcctg ggtggaccct     180
gagtaccgca agtggctcga agaggacgcg acggccgcga tggcgtcatt gggctatgcc    240
```

```
ggtgagcagg cacaccaaat ttcggcggtc ttcaacgact cccaaacgca tcacgtggtg    300
gtgtgcactc tgtgttcgtg ctatccgtgg ccggtgcttg gtctcccgcc cgcctggtac    360
aagagcatgg agtaccggtc ccgagtggta gcggaccctc gtggagtgct caagcgcgat    420
ttcggtttcg acatccccga tgaggtggag gtcaggggttt gggacagcag ctccgaaatc    480
cgctacatcg tcatcccgga acggccggcc ggcaccgacg gttggtccga ggaggagctg    540
acgaagctgg tgagccggga ctcgatgatc ggtgtcagta atgcgctcac accgcaggaa    600
gtgatcgtat ga                                                        612
```

<210> SEQ ID NO 2
<211> LENGTH: 203
<212> TYPE: PRT
<213> ORGANISM: Rhodococcus rhodochrous
<220> FEATURE:
<223> OTHER INFORMATION: alpha-subunit of nitrile hydratase of
      Rhodococcus rhodochrous

<400> SEQUENCE: 2

```
Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 3
<211> LENGTH: 690
<212> TYPE: DNA
<213> ORGANISM: Rhodococcus rhodochrous
<220> FEATURE:
<223> OTHER INFORMATION: beta-subunit of nitrile hydratase of
      Rhodococcus rhodochrous

<400> SEQUENCE: 3

```
atggatggta ccacgacac aggcggcatg accggatacg gaccggtccc ctatcagaag    60
gacgagccct tcttccacta cgagtgggag ggtcggaccc tgtcaattct gacttggatg   120
```

```
catctcaagg gcatatcgtg gtgggacaag tcgcggttct tccgggagtc gatggggaac    180
gaaaactacg tcaacgagat tcgcaactcg tactacaccc actggctgag tgcggcagaa    240
cgtatcctcg tcgccgacaa gatcatcacc gaagaagagc gaaagcaccg tgtgcaagag    300
atccttgagg tcggtacac ggacaggaag ccgtcgcgga agttcgatcc ggcccagatc     360
gagaaggcga tcgaacggct tcacgagccc cactccctag cgcttccagg agcggagccg    420
agtttctctc tcggtgacaa gatcaaagtg aagagtatga acccgctggg acacacacgg    480
tgcccgaaat atgtgcggaa caagatcggg gaaatcgtcg cctaccacgg ctgccagatc    540
tatcccgaga gcagctccgc cggcctcggc gacgatcctc gcccgctcta cacggtcgcg    600
ttttccgccc aggaactgtg gggcgacgac ggaaacggga agacgtagt gtgcgtcgat     660 ctctgggaac cgtacctgat ctctgcgtga                                     690
```

```
<210> SEQ ID NO 4
<211> LENGTH: 229
<212> TYPE: PRT
<213> ORGANISM: Rhodococcus rhodochrous
<220> FEATURE:
<223> OTHER INFORMATION: beta-subunit of nitrile hydratase of
      Rhodococcus rhodochrous

<400> SEQUENCE: 4

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
                100                 105                 110

Arg Lys Phe Asp Pro Ala Gln Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```